(12) United States Patent
Liu

(10) Patent No.: US 11,660,272 B2
(45) Date of Patent: May 30, 2023

(54) METHOD FOR COATING PARTICLES

(71) Applicant: University of Hertfordshire Higher Education Corporation, Hertfordshire (GB)

(72) Inventor: Fang Liu, Hertfordshire (GB)

(73) Assignee: University of Hertfordshire Higher Education Corporation, Hertfordshire (GB)

(*) Notice: Subject to any disclaimer, the term of this patent is extended or adjusted under 35 U.S.C. 154(b) by 8 days.

(21) Appl. No.: 16/755,032

(22) PCT Filed: Oct. 12, 2018

(86) PCT No.: PCT/GB2018/052940
§ 371 (c)(1),
(2) Date: Apr. 9, 2020

(87) PCT Pub. No.: WO2019/073257
PCT Pub. Date: Apr. 18, 2019

(65) Prior Publication Data
US 2020/0315979 A1    Oct. 8, 2020

(30) Foreign Application Priority Data
Oct. 12, 2017  (GB) ..................... 1716716

(51) Int. Cl.
*A61K 6/00*   (2020.01)
*A61K 9/50*   (2006.01)
*A61K 9/00*   (2006.01)

(52) U.S. Cl.
CPC .......... *A61K 9/5089* (2013.01); *A61K 9/5026* (2013.01); *A61K 9/5078* (2013.01); *A61K 9/0053* (2013.01)

(58) Field of Classification Search
None
See application file for complete search history.

(56) References Cited

U.S. PATENT DOCUMENTS

| 4,181,709 A * | 1/1980 | Dannelly ............. A61K 9/5026 424/482 |
| 4,960,244 A | 10/1990 | Maag et al. |
| 5,254,168 A | 10/1993 | Littman et al. |
| 5,411,745 A * | 5/1995 | Oshlack ............... A61K 31/485 424/490 |
| 7,906,145 B2 | 3/2011 | Castan et al. |
| 2003/0181421 A1 | 9/2003 | Horowitz et al. |
| 2004/0121003 A1 | 6/2004 | Chickering et al. |
| 2005/0265955 A1 | 12/2005 | Raman et al. |
| 2008/0000419 A1 | 1/2008 | Bender et al. |
| 2008/0254115 A1 | 10/2008 | Rubino |
| 2010/0034968 A1 | 2/2010 | Engels et al. |
| 2015/0352568 A1 * | 12/2015 | Maher .................. B05B 7/0075 118/310 |
| 2019/0099328 A1 * | 4/2019 | Zhu ..................... A23G 3/2076 |

FOREIGN PATENT DOCUMENTS

| WO | 9920255 A1 | 4/1999 |
| WO | 2010080970 A2 | 7/2010 |
| WO | 2011107855 A2 | 9/2011 |
| WO | 2017012935 A1 | 1/2017 |

OTHER PUBLICATIONS

Intellectual Property Office of the United Kingdom, Patents Act 1977: Combined Search and Examination Report under Sections 17 and 18(3), Application No. GB1716716.4, dated Oct. 4, 2018 (5 pages).
European Patent Office, International Search Report and Written Opinion of the International Searching Authority, International Application No. PCT/GB2018/052940, dated Jan. 25, 2019 (13 pages).
International Journal of Pharmaceutics, Dec. 2003, vol. 268, Issues 1-2, Pearnchob and Bodmeier, "Coating of pellets with micronized ethylcellulose particles by a dry powder coating technique", pp. 1-11.
Intellectual Property Office of the United Kingdom, Patents Act 1977: Search Report under Section 17(5), Application No. GB1606816.5, dated Jan. 27, 2017 (5 pages).
Intellectual Property Office of the United Kingdom, Patents Act 1977: Amendment to Search Report, Application No. GB1606816.5, dated Jun. 29, 2017 (3 pages).

* cited by examiner

*Primary Examiner* — Susan T Tran
(74) *Attorney, Agent, or Firm* — Wood Herron & Evans LLP

(57) ABSTRACT

Methods are provided for coating particles characterised by the addition of a powdered excipient, typically during coating. Typically, the coating method comprises Wurster fluidized bed coating. The method provides for coating particles in a coater comprising a coating processing chamber, wherein the particles comprise an active pharmaceutical ingredient. The coated particles are preferably for use in a method of administering an active pharmaceutical ingredient or for use in a method of treating or preventing a disease or condition. The invention further provides a pharmaceutical composition comprising coated particles obtainable by the method of the invention, preferably as part of a liquid formulation for oral administration.

46 Claims, 4 Drawing Sheets

METHOD FOR COATING PARTICLES

CROSS-REFERENCE TO RELATED APPLICATIONS

This application is a submission under 35 U.S.C. § 371 of International Application No. PCT/GB2018/052940, filed Oct. 12, 2018, which claims priority to Great Britain Application No. 1716716.4, filed Oct. 12, 2017, the disclosures of which are hereby expressly incorporated by reference herein in their entireties.

FIELD OF THE INVENTION

This invention relates to methods for coating particles characterised by the addition of a powdered excipient, typically during coating. Typically, the coating method comprises fluidised bed coating. The method is particularly applicable to coating microparticles, or particles in general with a modified drug release coating.

BACKGROUND OF THE INVENTION

Microparticles are well-known in pharmaceutical formulations for delivering active pharmaceutical ingredients. Microparticles comprising an active pharmaceutical ingredient or ingredients may be coated in order to modify the properties of the microparticles. For instance, the particles may have a functional coating that is resistant to breakdown inside the stomach (enteric-coated or gastric-resistant) but breaks down when in the intestine to release the medication. The coatings may also be configured for sustained release, releasing the medication over a period of time. Some medications are now administered as liquid formulations comprising coated microparticles dispersed in a liquid medium. These liquid formulations are easier for patients to swallow than tablets or capsules and therefore have particular utility in paediatric and geriatric populations. The coating may be a functional coating configured to provide modified-release formulations.

Particles may be coated in various ways, with fluidised bed coating (FBC) being a common method used. FBC is known for forming coated microparticles suitable for the liquid formulations discussed above, such as microparticles with a functional coating. FBC can be processed by top, bottom (Wurster) or tangential (rotor process) spray. Each of the mentioned methods is characterised by its own technological features: equipment/options, the coating process and process mode. Compared to the top spray or rotor process, the Wurster FBC combines a partition (column/cylinder) and an air distribution plate to organise the particle flow in close proximity to the spray nozzle. In Wurster FBC the droplets of the coating liquid travel only a short distance before being deposited onto the core particle. As a result, the coating is applied more evenly. The bottom (Wurster) spray FBC is the most commonly used coating process for the pharmaceutical industry due to its high coating uniformity and coating efficiency. In Wurster FBC, a processing column contains a bed of the particles to be coated and the bed is fluidised by an air stream that induces a cyclic particle flow. A spray nozzle is located at the bottom of the fluidised bed and the cyclic flow forces the particles upward past the nozzle through a Wurster cylinder. The nozzle sprays atomized droplets of a coating formulation in the same direction as the particle flow. The coating formulation comprises the coating ingredient and an organic solvent or aqueous coating vehicle. Passing particles move upward into an expansion zone as droplets of coating formulation deposit on their surfaces. The expansion zone reduces air velocity to allow particles to circulate back to the fluidised bed to a "down flow" zone outside the Wurster cylinder. The expansion zone also allows particles to further increase distance from one another temporarily to minimize particle agglomeration. The organic solvent or aqueous coating vehicle is evaporated as the particles move into and through the expansion zone to leave the non-volatile coating ingredients on the particle surface as part of the developing coating layer. The mostly dried particles flow through the "down flow" zone and are suctioned into the Wurster cylinder by air flow to pass the spray nozzle once again. Process parameters are set for optimal vehicle removal and film coat characteristics. This batch process is continued until particles are coated uniformly to the desired coat percentage, film thickness, or mass increase.

As stated above, microparticles comprising active pharmaceutical ingredients can be coated using FBC and administered as part of liquid formulations for ease of swallowing. U.S. Pat. No. 7,906,145 describes a ready-to use liquid suspension containing coated sustained-release microparticles. The coating formulation used to produce the sustained-release microparticles is based on ethyl cellulose (water insoluble polymer for controlling drug release) with an addition of poreformers (e.g. polyvinylpyrrolidone, water soluble polymer to form pores in the coat). The coating is applied to the particles by FBC using organic solvents in the coating formulation.

WO 2011/107855 A2 also describes a ready-to-use liquid suspension containing coated sustained release microparticles. The technology is composed of a complex coating system consisting of at least four coating layers on top of a microparticle core: 1) a seal coat; 2) a drug layer; 3) a controlled release polymer layer; and 4) a protective coating layer. The coating is applied to the particles by FBC using organic solvents in the coating formulation.

US2005/0265955 A1 describes sustained-release drug particles suitable for forming sustained-release oral formulations. The particles contain drug-ionic exchange resin complex and a water-permeable diffusion barrier using polymeric coatings. The coating is applied to the particles by FBC using water in the coating formulation.

WO 2017/012935 also describes a multi-layered coating system onto microparticles for liquid medicines with modified drug release e.g. gastric-resistance or sustained release. The coating system comprises at least 5-layers: 1) a separation layer; 2) a drug layer; 3) an intermediate layer; 4) a controlled release layer and 5) an outmost layer. The outmost layer contains hydrophilic and hydrophobic component and is able to keep the microparticles stable in aqueous media for one day to one month. The coating is applied to the particles by FBC using water or organic solvent in the coating formulation.

A drawback with coating small particles (microparticles, of diameter <1000 μm) by FBC is that the particles become tacky as the coating formulation dries. This tackiness can cause particles to stick together forming agglomerates. Agglomeration occurs when the coating ingredient has a strong binding strength, greater than the separation force exerted on the sprayed particles. The size of the particles is important as the smaller the particles that are coated, the higher the levels of agglomeration. This is due to an increased number density of the particles, increasing the prospect of forming a liquid bridge between the particles. A highly viscous coating formulation can be the primary reason for particle agglomeration. Furthermore, for the Wurster process, agglomeration can take place near the spray nozzle at the bottom of the fluidised bed as the nozzles generate the Venturi effect, resulting in particles being suctioned into the concentrated spray pattern. More importantly, when coating microparticles, the particles can become stuck in the "down flow" zone outside the Wurster cylinder where mostly dried particles are ready to be suctioned into the Wurster cylinder by air flow ready to be sprayed again. This is caused by tackiness of the coating and the strong inter-particular forces between small particles which reduces particle flowability. The stuck or non-flowing particles at the "down flow" zone can reduce air flow and consequently cause further particle agglomeration and/or uneven coating distribution among the particles. FIG. 1 illustrates the different zones in the Wurster fluidised bed.

Agglomeration of coated particles is undesirable for various reasons. The agglomerated particles are larger than the individual particles and may lead to a broader size distribution and different dissolution characteristics, impacting on drug bioavailability. The larger agglomerated particles may block the nozzles spraying the coating formulating into the processing column. For coated particles containing medication for use in liquid formulations, larger agglomerated particles may give the liquid formulation an unpleasant "gritty" texture when used. Furthermore, the larger agglomerated particles may sediment out of suspension before the smaller individual particles, potentially remaining in the drinking vessel after the liquid has been swallowed, making the dosage of the medication inside the particles hard to control. When particles stick to each other in the "down flow" zone outside the Wurster cylinder of FBC, these particles will not be sufficiently coated and thus will not provide effective function of the coating. Accordingly, there is a need to minimise the agglomeration of particles that occurs during FBC and to prevent particle sticking in the "down flow" zone in the FBC.

Prior art methods for minimising agglomeration include control of the process parameters of FBC, and adding further components to the coating formulation. For example, changing the plasticizer used in the coating formulation can result in a less sticky coating formulation, thus less agglomeration. Glidants may also be included in the coating formulation to reduce inter-particle friction and enhance the flow of the particle mixture, thus reducing agglomeration. US 2010/0034968 describes a method of coating particles using fluid bed rotor processor. In this method, undiluted polymer solution/dispersion without glidant is sprayed onto drug-containing cores. Glidant is introduced to the rotor chamber simultaneously and continuously to the polymer solution/dispersion to prevent agglomeration. The method can be applied to particles of 50-10,000 μm in diameter and a large quantity of glidant is used (10-100% w/w based on the amount of polymer). As the particles sequentially pass through the liquid polymer spray zone and the powder spray zone, a homogenous mixture of the glidant and polymer is achieved in the resultant film similar to the result of adding the glidant in the polymer coating liquid. US20150352568A1 describes an improved FBC Wurster apparatus with a spray gun assembly connecting to a source of dry powder, with an aim to prevent nozzle blockage or agglomeration caused by the presence of powdered ingredient in the spray liquid (e.g. excipients, active pharmaceutical substances or polymers). US2008/000419A1 attempts to improve particle flow during coating process in the "down flow" zone by modify the design of the coating chamber and the bottom perforated plate. However, there remains a need for further improvement in coating methods and further minimisation of agglomeration using Wurster FBC.

SUMMARY OF THE INVENTION

The inventors have unexpectedly found that for coating small particles (microparticles) of size range 10-1000 μm, preferably 10-500 μm and more preferably 10-250 μm, common methods of coating particles in a Wurster fluidised bed coater, can be improved by adding a small quantity of powdered excipient, such as a glidant, to the spray zone or drying zone of the processing column (for instance in the expansion zone or in the "down flow" zone) during the coating process. The improved method of the invention especially improves particle flow in the "down flow" zone of the processing column which results in less agglomeration of the coated microparticles and more even distribution of the coating applied onto the particles. The method of the invention is convenient for improving conventional Wurster FBC methods for applying a functional coating to microparticles comprising an active pharmaceutical ingredient because it does not require reformulation of a previously selected coating formulation chosen for particular desired characteristics.

Accordingly, in a first aspect, the invention provides a method for coating microparticles in a coater comprising a processing chamber, wherein the microparticles comprise an active pharmaceutical ingredient, the method comprising:
(i) adding microparticles to the processing chamber;
(ii) adding a coating formulation to the processing chamber through a first inlet; and
(iii) adding a powdered excipient to the processing chamber through a second inlet.

Steps (i), (ii), and (iii) may be carried out in any order or each simultaneously with any other step or steps. Steps (i), (ii), and (iii) may independently be carried out continuously or intermittently.

In one embodiment step (i) is carried out before steps (ii) and (iii). Steps (ii) and (iii) may be carried out in any order or simultaneously, preferably simultaneously. For instance, step (ii) may be carried out continuously whilst step (iii) is carried out continuously, intermittently or via a single addition. In one embodiment of the method of the invention the coater is a bottom spray (Wurster) fluidised bed coater. In other words the method is a bottom spray fluidised bed coating method. Typically, microparticles are added to the processing chamber which in this case would be a processing column and fluidised by the cyclic air stream in the processing column. A coating formulation is added to the processing column via the spray nozzle located at the bottom of the processing column and sequentially, or simultaneously (preferably simultaneously) the powdered excipient is added through a second inlet. The second inlet may be sufficiently separate from the first inlet; (for instance, the second inlet could be the inlet used for introducing the microparticles to the processing column to the drying zone of the processing column (such as the expansion zone or the "down flow" zone). Alternatively the second inlet could be adjacent to the first inlet, for instance, using a single spray nozzle which has separate outlet ports. While the addition of the coating formulation is typically continuous during the processes, the addition of the powdered excipient may be continuous, intermittent, or via a single batch. Additional microparticles may optionally be added either continuously, intermittently, or in a single batch during the process.

Thus, in a second aspect, the invention provides a method for coating microparticles in a Wurster (bottom spray)

fluidised bed coater comprising a processing column and a spray nozzle, wherein the microparticles comprise an active pharmaceutical ingredient, the method comprising:
(i) adding microparticles to the processing column to provide a fluidised stream of microparticles in the processing column;
(ii) coating the microparticles by adding a coating formulation to the processing column through the spray nozzle; and
(iii) adding a powdered excipient to the processing column through a second inlet.

In this second aspect, step (i) is carried out before step (ii). Step (iii) may be carried out before, during or after step (ii). Preferably step (iii) at least partially coincides with step (ii).

The inventors also unexpectedly found that the step (iii) of the invention assists the control of the drug release from particles coated with controlled- (sustained-, extended- or slow) release polymers. This is due to the hydrophobic nature of the powdered glidants added in step (iii) of the invention. For particles coated with controlled- (sustained-, extended- or slow) release polymers, the polymer forms a membrane surrounding the core which contains the Active Pharmaceutical Ingredient (API). The membrane is usually insoluble but permeable in aqueous media, for instance the gastrointestinal fluid. Drug release from coated particles is controlled by diffusion of the drug through continuous polymer phase, plasticizer channels and aqueous pores. It is commonly known that addition of hydrophobic components to the coating can slow down the drug release rate. However, surprisingly, the addition of powdered glidants in step (iii) of the invention did not follow the expected magnitude of reduction in the drug release rate as a response to the increasing concentration of hydrophobic components in the membrane, typically observed when glidants are added to the coating formulation in step (ii). The addition of glidants in this manner is at least 2-5 times more effective in decreasing drug release rate compared to the conventional method of adding glidant in the coating formulation. It is believed that this effect is related to the disruptive pattern of the location of the powdered glidant in the resultant coating, particularly but not limited to when the powdered glidant was added in an intermittent manner. As a high concentration of glidant is located in intermediate layers in the coating, the diffusion pathway of the API from the core is interrupted by this highly hydrophobic layer and drug release rate was slowed down to unexpected level. This is advantageous as the improved control in drug release reduces the level of coating thickness that is required to achieve a desired drug release rate and subsequent the length of maintaining in therapeutic effective drug plasma concentration for instance for 8, 12 or 24 hours. This effect applies to particles of size range 10-10,000 μm diameter and is not limited to microparticles.

Thus, in a third aspect, the invention provides a method for coating particles with a controlled drug release coating in a Wurster (bottom spray) fluidised bed coater comprising a processing column and a spray nozzle, wherein the particles comprise an active pharmaceutical ingredient, the method comprising:
(i) adding particles to the processing column to provide a fluidised stream of particles in the processing column;
(ii) coating the particles with a controlled drug release coating by adding a controlled drug release coating formulation to the processing column through the spray nozzle; and
(iii) adding a powdered excipient to the processing column through a second inlet.

In this third aspect, step (i) is carried out before step (ii). Step (iii) may be carried out before, during or after step (ii). Preferably step (iii) at least partially coincides with step (ii).

In this third aspect, preferably at least 80% w/w of the particles to be coated have a particle size range of 10-10,000 μm preferably measured using sieve analysis.

In each of the above aspects, the powdered excipient comprises or consists of a pharmaceutically acceptable glidant such as talc, kaolin, bentonite, stearic acid, glycerol monostearate, zinc stearate, magnesium stearate, calcium stearate, aluminium monostearate, glyceryl stearate, glyceryl palmitostearate, sodium stearyl fumarate, magnesium silicate, calcium silicate, magnesium aluminium silicate, silicon dioxide, colloidal silicon dioxide, hydrophobic colloidal silica, aluminium oxide, magnesium oxide, titanium dioxide, calcium carbonate, magnesium carbonate, calcium phosphate, and combinations thereof. In one embodiment the powdered excipient comprises or consists of magnesium stearate. In another embodiment the powdered excipient comprises or consists of silicon dioxide. In yet another embodiment the powdered excipient comprises or consists of combination of magnesium stearate and silicon dioxide.

The powdered excipient is preferably added as a dry powder. In some cases the dry powder has a moisture content of less than 6%, or 3%, or 1% by weight. Dry could also be understood to mean powders which are dry to the touch. The powder can be dry whilst having water absorbed or adsorbed to it, for example, if the excipient is a hygroscopic material.

The median particle size of the powdered excipient is preferably in the range of greater than 0.1 to 200 μm, or 0.1-100 μm, or 1-50 μm, or about 10 μm, typically measured using Laser Diffraction Particle Size Analysis and expressed as the median diameter ($D_{50}$). For the avoidance of doubt, the term "particle size" as used in the context of the powdered excipient refers to the equivalent spherical diameter (esd), i.e. the diameter of a sphere having the same volume as a given particle. The terms "median particle size" or "$D_{50}$" refer to the volume-based median particle diameter, i.e. the diameter below which 50% by volume of the particle population is found.

In one embodiment the coating formulation comprises a polymer and the powdered excipient is added in amounts of 0.1-50% or 0.5-20% or 0.5-10-% w/w based on the weight of the dry polymer in the coating formulation.

In one embodiment the coating formulation in step (ii) is added to a first region of the processing column, e.g. the region adjacent to a spray nozzle of a fluidised bed coater, and the powdered excipient in step (iii) is added to a second region of the processing column and the first and second regions are adjacent or substantially separate to each other.

Typically, the coated particles or microparticles obtainable by the invention are pharmaceutically acceptable. Preferably, therefore, the ingredients in the process will also be pharmaceutically acceptable.

Typically, particle size can be measured using Laser Diffraction Particle Size Analysis. The technique utilises diffraction of the laser light resulting from the interaction of the light with the particles. For a single spherical particle, the diffraction pattern shows a typical ring structure depending on the size of the particle. Simultaneous diffraction on more than one particle results in a pattern of scattered light with varied density and angle reflecting the particle size distribution. Particle size measured using this technique is typically expressed as "median particle size" or "$D_{50}$" referring to the volume-based median particle diameter, i.e. the diameter below which 50% by volume of the particle population is found. However, if particles stick together laser diffraction measures the size of the agglomerate rather than the size of the primary particles. Therefore, a single particle size parameter such as $D_{50}$ may not suitably represent particle populations that include agglomerated particles, as the single parameter may not reflect the degree of particle agglomeration.

In this invention, the particle size of the particles or microparticles and coated particles or microparticles is measured using sieve analysis by applying a range of analytical sieves. In this method, particles are put through a series of analytical test sieves mounted on an analytical sieve shaker (AS200, Retsch® GmbH). The opening diameters of the sieves are 2000, 1400, 1000, 710, 500, 355, 250, 180, 125, 90, and 50 µm. The sieves are shaken for 10 minutes. Particles remaining on each sieve are collected and weighed to give a percentage by total particle mass present at each particle size range (e.g. >2000, 2000-1400, 1400-1000 µm etc.).

In the first and second aspects of the invention preferably at least 80% w/w of the microparticles to be coated have a particle size range of 10-1000 µm, or 10-350 µm, or 10-200 µm, preferably measured using sieve analysis.

In a fourth aspect of the invention, the invention provides coated microparticles obtainable by the process for coating microparticles of the invention. In one embodiment at least 80% w/w of the coated particles have a particle size range of 20-1200 µm, or 20-400 µm, or 20-250 µm, preferably measured using sieve analysis.

In a further fifth aspect of the invention, the invention provides coated microparticles obtainable by the process for coating microparticles of the invention for use in a method of administration of an active pharmaceutical ingredient or for use in a method of treating or preventing a disease or condition. The invention further provides coated microparticles for use in therapy obtainable by the process for coating microparticles.

In a further sixth aspect of the invention, the invention provides coated controlled drug release particles obtainable by the process for coating particles with a controlled drug release coating of the invention for use in a method of administering an active pharmaceutical ingredient or for use in a method of treating or preventing a disease or condition. The invention further provides coated controlled drug release particles for use in therapy obtainable by the process for coating particles with a controlled drug release coating.

The invention further provides a pharmaceutical composition comprising the coated microparticles obtainable by the process for coating microparticles of the invention and a pharmaceutically acceptable excipient. Preferably the pharmaceutical composition is a liquid suspension. The pharmaceutical composition may also be in the form of a powder for mixing with a liquid before administration to patients, i.e. a powder for reconstitution into a liquid. Furthermore, the pharmaceutical composition may also be in the form of a MUPS (multi-unit pellet system) tablet, capsule or an dispersible/orally dispersible tablet.

BRIEF DESCRIPTION OF THE DRAWINGS

Other aspects and features of the present invention will become apparent to those ordinarily skilled in the art upon review of the following description of specific embodiments of the invention in conjunction with the accompanying figures.

FIG. 5. illustrates a chart showing the drug release from 50% gliclazide loaded Cellets® 100 which are coated with 25% coating level (C.L.) with Eudragit® NM and with 100% talc as glidant, with and without magnesium stearate added as dry powder during coating process. Magnesium stearate is abbreviated as Mg St.

DETAILED DESCRIPTION OF THE INVENTION

Figure 1:
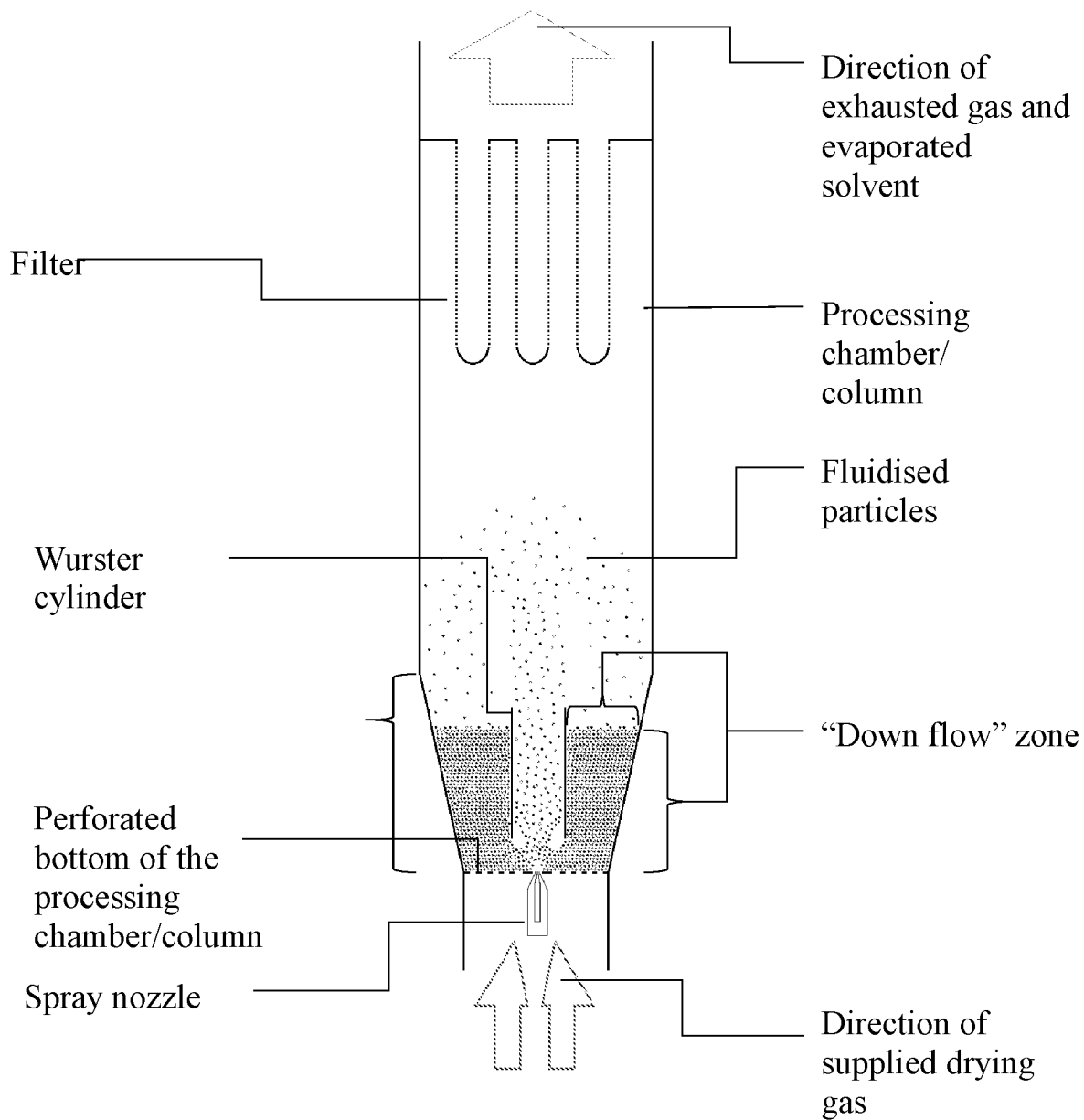
FIG. 1 illustrates the different zones in the Wurster fluidised bed.

In typical FBC particles to be coated are added to a processing column through a loading or charging port, which typically works by pneumatically moving the particles by a combination of pressure differential and the flow of a gas, such as air. The particles to be coated may be added to the processing column by other means depending on the equipment used, as is known in the art. The particles are then fluidised and a coating formulation is added to the processing column through a first inlet such as a spray nozzle or a group of spray nozzles. The coating formulation contains the material, typically a polymer, to be coated onto the fluidised particles. The coating formulation may comprise further components such as plasticisers, glidants, emulsifiers, organic or inorganic salts, and liquids such as water or organic solvents. The Wurster FBC equipment is typically set up with spray nozzle(s) located at the bottom of a fluidised bed of particles with a cyclic air flow forcing the particles upward past the nozzle outflow within a Wurster cylinder. The nozzle sprays atomized droplets of the coating formulation continuously with particle flow. Passing particles move upward into an expansion region as droplets of coating formulation deposit on their surfaces and circulate back to the fluidised bed "down flow" zone outside the Wurster cylinder. The coating formulation is sprayed into the processing column through the Wurster cylinder until the particles are coated to the desired level. This is also known as the Wurster coating process. The skilled person will know when the desired level is achieved based on the desired properties of the coated particles and from their general knowledge. If necessary, samples can be taken and/or test batches can be prepared to help identify the desired level of coating. When this desired level is achieved no more coating formulation is added to the processing column and the coated particles are removed. The coating applied to the particles can be measured by a mass gain relative to the uncoated particles and can be expressed as a percentage weight gain.

The present invention can use typical FBC setups but requires a powdered excipient to be added to the processing column through a second inlet during the coating process. Step (i) of the invention involves the addition of microparticles to a processing column by any means, as is known in the art. The microparticles are then fluidised. Step (ii) involves the addition of a coating formulation to the processing column through a first inlet such as a spray nozzle or nozzles, as is also known in the art. Such coating formulations often contain glidant (anti-tacking agent) to prevent agglomeration. The inventors have found that for coating small particles (microparticles of diameter <1000 μm), adding glidant in step (ii) of the invention is not sufficient to prevent particle agglomeration and ensure even distribution of the coating onto the particles. The effectiveness of increasing the concentration of glidants in the coating formulation to improve coating process and prevent agglomeration reaches a plateau. Further increasing glidant concentration in the coating formulation does not prevent further agglomeration in the case of small particles. The inventors have unexpectedly found that step (iii) of the invention, adding a small quantity of powdered excipient, typically a glidant, to the processing column through a second inlet in the spray zone or drying zone of the processing column during the coating process, dramatically improves coating process and prevents particle agglomeration. This method particularly improves particle flow in the "down flow" zone, which prevents particles getting stuck in this area and the consequent of reduction in air flow. This results in a lower incidence of particle agglomeration and a more even distribution of the coating onto the particles. For coating microparticles, the improvement to the coating process by step (iii) of the invention does not follow the typical relationship between the concentration of glidants in the coating formulation and the effectiveness of preventing particle agglomeration and improving coating process, as shown in conventional methods of adding glidants as part of the coating formulation added in step (ii) of the invention or adding glidants separately with undiluted polymer solution/dispersion to the processing column to form a homogenous coating layer as described in US 2010/0034968. Using the method of step (iii) of the invention, a small quantity of glidant is required to be added to the drying zone of the processing column. However, the effect of improving the coating process and preventing particles sticking in the "down flow" zone and agglomeration of small particle coating is approximately 10 times more efficient than conventional or other known methods of using glidants in the coating as described above. This is unexpected and surprising. It is believed that by adding powdered excipient to the spray zone or processing column (for instance in the expansion zone or in the "down flow" zone) through the second inlet as shown in step (iii) of this invention, the powdered glidant is not homogenously mixed with the polymer used in the resultant coating as usually occurs in the conventional methods and the method described in US 2010/0034968. Instead, the powdered glidant forms a surface coating on dried (in the pressing column) or partially dried particles (in the spray zone) and the deposition of the powdered glidant and the polymer are in a disrupted pattern. This is particularly apparent when the powdered glidant is added in an intermittent manner, whereby a concentrated layer of dry glidant is located at the outer surface of the dried or partially dried particles and thus is more effective in reducing the inter-particular cohesive forces and improving the flowability at the "down flow" zone of the processing column. The improved particle flow in the "down flow" zone of the processing column prevents particle sticking in this region and prevents reduction in air flow by air paths becoming blocked and thus prevents particle agglomeration. This also prevents uneven distribution of the coating onto particles.

The step (iii) of this invention is particularly suitable for Wurster FBC whereby there are clear distinct drying and liquid spray zones. When particles pass through the liquid spray zone, droplets of the liquid coating formulation, typically containing glidants in the formulation to prevent particle agglomeration in this zone, deposits onto the particles. In the drying zone (for instance the expansion zone), solvent evaporates from the particle surface and the coated particles are at least partially dried when the powdered glidant comes into contact with the particles. It is possible that, in Wurster FBC even when the dry powder glidant is added in the spray zone, the powdered glidant can come into contact with the particles when it is partially dried and thus obtain similar effect in improving particle flow in the "down flow" zone. This is a distinct feature from tangential (rotor) process, where no distinct drying zone is present.

In another aspect of the invention, the inventors also unexpectedly found that the step (iii) of the invention assists the control of the drug release from particles coated with controlled- (sustained-, extended- or slow) release polymers. This is due to the hydrophobic nature of the powdered glidants added in step (iii) of the invention. For particles coated with controlled- (sustained-, extended- or slow) release polymers, the polymer forms a membrane surrounding the core which contains the API. The membrane is usually insoluble but permeable in aqueous media, for instance the gastrointestinal fluid. Drug release from coated particles is typically controlled by diffusion of the drug through continuous polymer phase, plasticizer channels and aqueous pores. It is commonly known that addition of hydrophobic components to the membrane slows down drug release rate. However, surprisingly, the addition of powdered glidants in step (iii) of the invention did not follow the expected magnitude of reduction in the drug release rate as a response to the increasing concentration of hydrophobic components in the membrane, typically observed when glidants are added to the coating formulation in step (ii). The addition of glidants in this manner is at least 2-5 times more effective in decreasing drug release rate compared to the conventional method of adding glidant in the coating formulation. It is believed that this effect is again related to the disruptive pattern of the location of the powdered glidant in the resultant coating, particularly but not limited to when the powdered glidant was added in an intermittent manner. As a high concentration of glidant is located in intermediate layers in the coating, the diffusion pathway of the API from the core is interrupted by this highly hydrophobic layer and drug release rate was slowed down to unexpected level. This is advantageous as the improved control in drug release reduces the level of coating thickness that is required to achieve a desired drug release rate and subsequent the length of maintaining in therapeutic effective drug plasma concentration for instance for 8, 12 or 24 hours. This effect applies to particles of size range 10-10,000 μm diameter and is not limited to microparticles.

The powdered excipient is preferably added as a dry powder, which may be dry to the touch.

The powdered excipient can comprise or consist of a glidant or mixtures of glidants such as talc, kaolin, bentonite, stearic acid, glycerol monostearate, zinc stearate, magnesium stearate, calcium stearate, aluminium monostearate, glyceryl stearate, glyceryl palmitostearate, sodium stearyl fumarate, magnesium silicate, calcium silicate, magnesium aluminium silicate, silicon dioxide, colloidal silicon dioxide, hydrophobic colloidal silica, aluminium oxide, magnesium oxide, titanium dioxide, calcium carbonate, magnesium carbonate, calcium phosphate. The preferred glidants for use in the invention are magnesium stearate and/or silicon dioxide.

It is preferred that the powdered excipient is added in amounts of 0.1-50% or 0.5-20% or 0.5-10% w/w based on the weight of the dry polymer in the coating formulation. The total amount of the powdered excipient to be added this way can be supplied continuously to the spray zone or processing column during the coating process at a suitable rate until the completion of the coating. Alternatively, the total amount of the powdered excipient to be added this way can be divided into portions and supplied to the spray zone or processing column at predetermined intervals such as one portion every 1-90 minutes during coating. The total amount can also be added in a single addition at a predetermined point during coating.

It is preferred that the powdered excipient has a median particle size of greater than 0.1 to 200 µm, or 0.1-100 µm, or 1-50 µm, or about 10 µm, as measured using Laser Diffraction Particle Size Analysis.

The powdered excipient is added to the spray zone or processing column through a second inlet. It is possible that the second inlet is adjacent to the first inlet that the coating formulation is added through. In this case, the powdered excipient is added to the spray zone of the Wurster FBC. Alternatively, it is possible that the second inlet is distinctly located (far apart) from the first inlet. In this case, the second inlet may be on the top, bottom, or sides of the processing column. It is to be understood that through this type of second inlet, the powdered excipient is added to the processing column, for instance the expansion zone or the "down flow" zone.

When the second inlet is adjacent to the first inlet, the second inlet can be a separate spray gun (nozzle) or a separate region from the first inlet in a single spray gun (nozzle) assembly, located at the bottom of the Wurster cylinder. When the second inlet is distinctly located (far apart) from the first inlet, the second inlet can be a loading or charging port of the processing column which is typically located in the middle range of the processing column. The loading port can be the inlet via which the particles to be coated are added to the processing column in step (i) of the invention. In this embodiment, the powdered excipient is added to the loading or charging port, which typically works by pneumatically moving the powdered excipient by a combination of pressure differential and the flow of a gas, such as air, or by gravity.

It is preferred that the powdered excipient is added without interrupting the coating process, for example, without substantially changing the temperature in the coating region (or the product temperature as typically defined in the field of art), or the air pressure inside the processing column.

According to the invention, the coating formulation is added in step (ii) from the first inlet into a first region of the processing column, and the powdered excipient is added in step (iii) from the second inlet into a second region of the processing column, when the first and second regions are adjacent to each other or substantially separate. For example, the powdered excipient is added through the second inlet to the spray zone of the Wurster FBC. During this process, it is possible that the powdered excipient only comes into contact with the coated particles when they are partially dried. Alternatively, the powdered excipient is added through the second inlet to the processing column outside of the spray zone. In this case the powdered excipient, or the majority or substantially all of this powdered excipient, does not come into contact with the coating formulation (spray liquid) before this powdered excipient has come into contact with the particles being coated.

The first region may be defined by a tube open at both ends positioned above the spray nozzle(s) that form the first inlet. In this case, the second region can be the same as the first region or is outside the tube and may comprise an expansion zone of the processing column where the particles move further apart from each other and volatile components of the coating formulation evaporate to leave behind the developing coating layer.

The Particles to be Coated

The invention may be used to coat particles or microparticles comprising an API to form coated particles or microparticles. When the invention is used to coat microparticles, the coated microparticles are preferably suitable for liquid modified-release formulations.

The API is not limited to a particular type, and may be selected from the group of analgesics, antacids, antiulcerants, anti-Alzheimer's agents, anti-asthmatics, anti-hepatitis agents, anti-hypertensives, anti-inflammatory agents, anti-anginals, anti-arrhythmics, antibiotics, anticoagulants, anti-thrombotics, antidiabetics, antifungals, antiglaucoma agents, appetite suppressants, antiparasitics, antiepileptics, antiallergics, antidepressants, antihistamines, antivirals, antiparkinsonisms, diuretics, neuroprotectives, hypnotics, and combinations thereof.

The API is not limited to a particular ingredient and can be selected from acamprosate, aspirin, bisacodyl, budesonide, diclofenac, didanosine, erythromycin, lansoprazole, omeprazole, esomeprazole, ibuprofen, pantoprazole, rabeprazole, mesalazine, mycophenolic acid, naproxen, prednisolone, rowachol, rowatinex, sodium valproate, sulfasalazine, valproic acid, fentanyl, nifedipine, paracetamol, alprazolam, zolpidem, dalfampridine, cyclobenzaprine, bupropion, risedronate, morphine, morphine sulphate, hydromorphone, clarithromycin, verapamil, carbamazepine, nicardipine, diltiazem, doxazocin, ciprofloxacin, colestipol, methylphenidate, dexmethylphenidate, carvedilol, pancrelipase, duloxetine, divalproex, tolterodine, dexlansoprazole, diltiazem, isosorbide, oxybutynin, isradipine, venlafaxine, darifenacin, ferrous sulphate, metronidazole, tamsulosin, metformin, glipizide, gabapentin, propranolol, indomethacin, guanfacine, paliperidone, sitagliptin, clonidine, levetiracetam, telithromycin, desvenlafaxine, potassium, potassium chloride, lamotrigine, fluvastatin, ambrisentan, hyoscyamine, lithium, brompheniramine, fluvoxamine, pyridostigmine, pramipexole, guiafenesin, mycophenolate, mirabegron, memantine, nicotinic acid, orphenadrine, disopyramide, posaconazole, tapentadone, trazodone, oxycodone, paroxetine, felodipide, fluoxetine, ranolazine, galantamine, ropinirole, propafenone, tramadol, quetiapine, levodopa, carbidopa, minocycline, nisoldipine, hyoscyamine, dimethyl fumarate, theophylline, metoprolol, trimetazidine, thiotriazoline, meldonium, fesoterodine, pentoxifylline, fenofibric, acetaminophen, alfuzosin, nevirapine, albuterol, alpraxolam, hydrocodone, zileuton, ranitidine, cimetidine, atenolol, and salbutamol, and combinations thereof.

It is preferred that at least 80% w/w of the particles to be coated have a particle size range of 10-1000 μm, or 10-350 μm, or 10-200 μm, as measured using sieve analysis. Optionally, at least 90% w/w of the particles to be coated have a particle size range of 10-1000 μm, or 10-350 μm, or 10-200 μm, as measured using sieve analysis. Optionally, 100% w/w of the particles to be coated have a particle size range of 10-1000 μm, or 10-350 μm, or 10-200 μm, as measured using sieve analysis.

In the alternative preferably at least 80% w/w of the particles to be coated have a particle size range of 10-10,000 μm preferably measured using sieve analysis.

The particles to be coated may comprise an inner core and optionally a drug layer as a coating. The inner core in one alternative comprises a drug-containing core, in another alternative the inner core is inert and does not comprise any drugs. If the inner core comprises a drug containing core then the optional drug layer may not be present. However, if the inner core is inert and does not comprise any drugs then the optional drug layer will be present.

The drug-containing core can be obtained by layering active ingredients onto inert particle cores, or produced by granulation, extrusion-spheronization, hot-melt extrusion with following cooling down and cutting, melt-spray-congealing, spray-drying, solvent evaporation/extraction, adsorption onto ionic resins, coacervation or ionotropic gelation, dispersion polymerisation, precipitation (incl. precipitation from supercritical fluid) or alternatively drug crystals can be used. The inert particle cores include microcrystalline cellulose spheres, sugar spheres also known as nonpareil seeds, tartaric acid pellets, mannitol spheres, dibasic calcium phosphate beads and natural wax based spheres.

The drug layer may be coated onto the inner particle core. The drug layer contains APIs, a binding agent and one or more other pharmaceutically acceptable excipients. The binding agent is selected from the group comprising of starch, pregelatinized starch, gelatine, tragacanth, alginic acid, sodium alginate, acacia, polyvinyl pyrrolidone, polyvinyl alcohol, hypromellose, hydroxypropyl cellulose, methyl cellulose, ethyl cellulose, sodium carboxymethyl cellulose, microcrystalline cellulose, polyethylene glycol, polyethylene oxide, polypropylene glycol. The content of the active ingredient in the total coated particles may be in the range of 1-60% or 5-50% w/w of the total coated particles.

The Coating Formulation

The coating formulation contains the material, typically a polymer, to be coated onto the particles or microparticles in the processing column. The coating formulation may comprise further components such as plasticisers, glidants, emulsifiers, organic or inorganic salts, and liquids such as water or organic solvents.

When particles or microparticles containing an API are coated using the method of the invention the coating is preferably suitable to provide modified release of the API. Modified release can refer to gastric-resistant or sustained-release pharmaceutical dosage forms. Gastric-resistant dosage forms are also called "enteric coating" and "delayed release" and the terms are interchangeable. These dosage forms give no or very low levels of drug release in acidic conditions of the stomach (pH 1-4) and complete drug release when entering the intestine (pH 5-7 of the small intestine and pH 6-7.5 of the large intestine or colon). These dosage forms are used to 1) protect the stomach from irritant drugs; 2) prevent drug degradation in the acidic stomach conditions; or 3) targeting to specific sites in the gastrointestinal tract for optimal absorption or treatment for local diseases.

Sustained release is also referred to as "controlled release", "extended release", "slow release" and "prolonged release" and the terms are used interchangeably. Drug release from these formulations is typically pH-independent and occurs over an extended period compared to immediate release dosage forms. These can be used to provide once daily or twice daily administration, preferably once daily. Typically, the action of the API in sustained release formulations is limited by the rate of release of the API from the particles or microparticles rather than by the rate of uptake of the API by the patient.

For enteric coatings, the coating formulation and thus the coating layer contains pharmaceutically functional polymers either having pH-dependent or pH-independent dissolution. The coating layer forms a single coating layer surrounding the particle. The coating layer may represent 1-90%, 1-50% or 10-40% w/w of the total coated particles or microparticles.

The pH-dependent polymers suitable for modified-release coatings include polymethacrylates, e.g. Eudragit® L100, Eudragit® L100-55, Eudragit®L30D-55, Eudragit® L, Eudragit® S and Eudragit® FS 30D, Kollicoat® MAE, ACRYL-EZE® or the combination of these polymers, polyvinyl derivatives in particular polyvinyl acetate phthalate, cellulose-based polymers, e.g. cellulose acetate trimellitate, cellulose acetate phthalate, hypromellose phthalate, hypromellose acetate succinate, and natural occurring polymers such as shellac. These coatings are insoluble in low pH conditions of the stomach and soluble in higher pH conditions of the small intestine or the colon. Therefore, no or very low levels of drug release is expected in dissolution media of low pH levels (pH 1-4) and complete drug release when the media pH is changed to higher levels (pH 5.5-7 of the small intestinal pH and pH 6-7.5 of the large intestinal or colonic pH).

The pH-independent polymers suitable for modified-release coatings form a dissolution barrier surrounding the API-containing core. These polymers are insoluble in aqueous media regardless of the pH level but form a permeable membrane which allows the API in the core to diffuse through at a certain rate and thus providing a sustained drug release. Medicines containing these coated particles are expected to have prolonged therapeutic effects and allow once or twice daily administration. Polymers used in the coating include ethyl cellulose and its commercial dispersions such as SURELEASE® and AQUACOAT®, polymethacrylates e.g. Eudragit® RSPO/Eudragit® RS 30D and Eudragit® RLPO/Eudragit® RL 30D (especially the combination of the two), Eudragit® NE 30D/Eudragit® NE 40D. Water soluble components may be added to the coating formulation to create pores in the membrane during dissolution to further modify drug release rate. These can be low molecular weight materials such as sugars e.g. lactose or sucrose and silica, or water soluble polymers such as hypromellose, hydroxypropyl cellulose, polyvinyl alcohol, polyvinyl alcohol-polyethylene glycol graft copolymers, polyvinyl pyrrolidone and Eudragit EPO/Eudragit E100. The concentration ratio of the water soluble:insoluble polymer in the formulation can be in a range from 0:100 to 50:50, or 10:90 to 30:70.

Plasticizers may be included in the coating formulation to improve film formation, flexibility and to prevent cracking. Commonly used plasticizers for this purpose include triethyl citrate, polyethylene glycol (low to high molecular weights), acetyl triethyl citrate, acetyl tributyl citrate, polysorbate, dibutyl sebacate, triacetin, 1,2-propylene glycol, glycerin, diethylene glycol, triethylene glycol, tetraethylene glycol, sorbitol lactate, ethyl lactate, butyl lactate, and ethyl glycolate. The preferred plasticisers in this invention are triethyl citrate and polyethylene glycol at high molecular weights. Plasticisers can be included in amounts ranging from 5-40% or 5-25% or 10-20% w/w based on the total mass of dry polymer in the coating formulation.

Glidants and anti-tacking agents may be included in the coating formulation to help minimise particle agglomeration, in addition to the powdered excipient added through the second inlet in step (iii) of the invention. Typical glidants to be used are talc, glycerol monostearate, magnesium stearate, calcium stearate, glyceryl stearate, stearic acid, colloidal silicon dioxide, magnesium silicate, calcium silicate, mineral oil, sodium stearyl fumarate, glyceryl palmitostearate, zinc stearate, magnesium oxide, calcium phosphate, silicon dioxide, and combinations thereof. Talc can be used at 1-150%, or 50-150%, or 50-100% w/w based on the total mass of dry polymer in the coating formulation. Glycerol monostearate can be used at 0.1-100% or 5-50%, or 15-35% w/w based on the total mass of dry polymer in the coating formulation.

An emulsification agent such as polysorbate 80 or sodium lauryl sulphate may be included in the coating formulation to assist the emulsification of the glidant, for example, when glycerol monostearate is the glidant. The emulsification agent may be included in amounts of 0-20% w/w or 0.1-15% w/w or 0.1-10% w/w based on the total mass of dry polymer in the coating formulation.

An organic or inorganic salt maybe added to the coating formulation to help minimise particle agglomeration. The agglomeration of particles is associated with the viscosity of the spray solution or dispersion. The addition of a salt in the spray solution or dispersion decreases the viscosity due to the salting-out effect on the polymer and thus reducing the tendency of particle agglomeration. Controlled salting-out can be achieved by adding a low concentration of salt, so that it will not affect the polymer particle size in the initial spray solution or dispersion and not affect the droplet size when sprayed through the nozzle. However, during drying of the spray solution or dispersion in the coating process, the concentration of the salt increases and salting out can occur and decrease the viscosity of the drying polymer solution or dispersion. Inorganic salts that can be used for this purpose in the coating solution include the sodium, potassium, magnesium and calcium salt of the following acids, hydrochloric acid, chloric acid, sulphurous acid, sulphuric acid, persulfuric acid, disulfurous acid, tetrathionic acid, hydrosulfuric acid, nitric acid, nitrous acid, hydronitric acid, carbonous acid, hypocarbonous acid, carbonic acid, percarbonic acid, acetic acid, phosphorous acid, phosphoric acid, hypophosphoric acid, bromous acid, hydrobromic acid, bromic acid, hypobromous acid, fluorous acid, hypofluorous acid, hydrofluoric acid, fluoric acid, perfluoric acid, formic acid, tetraboric acid, boric acid, and siliceous acid. Organic salts that can be used for this purpose in the coating solution include the sodium, potassium, magnesium and calcium salt of the following acids, benoic acid, malonic acid, tartartic acid, phthalic acid, barbituric acid, cinnamic acid, glutaric acid, hexanoic acid, malic acid, folic acid, propanoic acid, glycolic acid, stearic acid, trifluoroacetic acid, scorbic acid, citric acid, isocitric acid, succinic acid, glutaric acid, azelaic acid, benzoic acid, fumaric acid, adipic acid, gluconic acid, lactic acid, oleic acid, propiolic acid, uric acid, acetic acid, gallic acid, lauric acid, caprylic acid, caprinic acid, and myristic acid. The preferred salt for this is sodium chloride. The salt can be added to the solution or dispersion at 0.01-20%, or 0.1-10%, or 0.1-5% w/w based on the total mass of dry polymer in the coating formulation.

The coating formulations can be prepared either as aqueous dispersion or organic solvent based solutions of the coating polymer. Solvents that can be used include water, ethanol, methanol, isopropanol, acetone, diethyl ether, methylene chloride, chloroform, n-butanol, methyl glycol, butyl glycol and ethyl acetate. Aqueous dispersions in water are preferred for this invention. The amount of solvent used in the formulation will depend on the solvent type and the amount of total solid (including all other components in the formulation other than the solvent) in the final coating formulation. In this invention, the percentage total solid (which means all components including liquids except solvents) in the coating formulation is preferably in the range of 1-50%, or 5-30%, or 10-25% w/w, the remainder being the solvent.

The Coating Process

The method of the invention is preferably performed using fluidised bed coating in a bottom spray (Wurster) arrangement. The equipment is set up as such to promote air flow and thus minimise particle agglomeration. It is recommended to use a sufficient drying air (nitrogen or other inert gas) volume to evaporate water or solvent effectively. The drying air capacity can be in the range of 0.5-2.5 $m^3$/min/kg or 1.0-2.0 $m^3$/min/kg, where "kg" refers to the weight of the particles to be coated. The atomising pressure for such coating can be used from 0.8-1.5 to 3.5 bar or 2.5 to 3.5 bar. The spray rate can be in the range from 5-20 g/min/kg or 8-16 g/min/kg. The inlet and product temperatures may be chosen according to the polymer used and are within the knowledge of a skilled person in the art.

The Coated Particles

The invention provides coated microparticles obtainable by the method of the invention. It is preferred that at least 80% w/w of the coated particles have a particle size range of 20-1200 μm, or 20-400 μm, or 20-250 μm, as measured using sieve analysis. Optionally, at least 90% w/w of the coated microparticles have a particle size range of 20-1200 μm, or 20-400 μm, or 20-250 μm, as measured using sieve analysis. Optionally, 100% w/w of the coated microparticles have a particle size range of 20-1200 μm, or 20-400 μm, or 20-250 μm, as measured using sieve analysis and/or laser diffraction method.

The invention also provides coated particles obtainable by the method of the third aspect of the invention. It is preferred that at least 80% w/w of the coated particles have a particle size range of 20-12,000 μm preferably measured using sieve analysis and/or laser diffraction method.

It is preferred that the coating layer is a functional coating suitable for modified release. The coating layer preferably represents 1-90%, 1-50% or 10-40% w/w of the total coated particles or microparticles.

It is preferred that the coated particles are suitable for use in a method of administering the API that is part of the particles, and thus are suitable for use in a method of treating or preventing a disease or condition. In this regard the coated particles are preferably suitable for dispersion in a liquid medium suitable for human or animal consumption and can form part of a liquid formulation for administering the API. Other methods of administration may be used. For example, the coated particles may also be suitable for sprinkling on to food to be eaten by the patient in order to administer the API.

Treatment of Diseases and Conditions

The invention further provides a pharmaceutical composition comprising coated particles or microparticles in combination with a pharmaceutically acceptable excipient.

The invention further provides a method for the treatment of a disease or condition, comprising the step of administering a therapeutically effective amount of coated particles or microparticles. The invention also provides the use of coated particles or microparticles in the manufacture of a medicament for the treatment of a disease or condition. The invention also provides coated particles or microparticles for use in treating a disease or condition.

Patient Populations

The coated particles or microparticles of the invention are of particular use for administering an active pharmaceutical ingredient to patients who find it difficult to swallow or dislike swallowing tablets or capsules, such as older adults or children. Older adults are at high risk of developing impairments in swallowing functions (known as dysphagia) due to the decline in neuromuscular function and muscle mass relating to deglutition and the widespread of co-morbidity and resultant polypharmacy. It has been estimated that 70-90% of the older population experience some degree of dysphagia. More than eighty percent of residents in care homes have mealtime difficulties related to swallowing and majority of these show signs of dysphagia. The prevalence of dysphagia is particularly high in patients with certain diseases such as Parkinson's disease (80%), Alzheimer's disease (40-70%), acute stroke (50%) and head and neck cancer (50%). Furthermore, some children do not like to swallow tablets or capsules, or have immature physiologies which makes swallowing relatively large objects difficult, but are willing or able to swallow liquid formulations.

Therapeutic Definitions

As used herein, "treatment" includes curative and pro-phylactic treatment. As used herein, a "patient" means a human or animal in need of treatment.

The amount of the coated particles or microparticles of the invention administered should be a therapeutically effective amount where the coated particles or microparticles are used for the treatment of a disease or condition and a prophylactically effective amount where the coated particles or microparticles are used for the prevention of a disease or condition.

The term "therapeutically effective amount" used herein refers to the amount of the active pharmaceutical ingredient contained in the coated particles or microparticles needed to treat or ameliorate a targeted disease or condition. The term "prophylactically effective amount" used herein refers to the amount of the active pharmaceutical ingredient contained in the coated particles or microparticles needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

Administration & Formulation

For pharmaceutical use, the coated particles or microparticles of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The coated particles or microparticles should be assessed for their biopharmaceutical properties, such as solubility and solution stability (across pH), permeability, etc., in order to select the most appropriate dosage form and route of administration for treatment of the proposed indication.

The coated particles or microparticles of the invention may be administered alone or in combination with one or more other coated particles or microparticles of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
- diluents, e.g. lactose, dextrose, sucrose, mannitol, sorbitol, cellulose and/or glycine;
- lubricants, e.g. silica, talc, stearic acid, its magnesium or calcium salt and/or polyethyleneglycol;
- binders, e.g. starch, pregelatinized starch, gelatine, tragacanth, alginic acid, sodium alginate, acacia, polyvinyl pyrrolidone, polyvinyl alcohol, hypromellose, hydroxypropyl cellulose, methyl cellulose, ethyl cellulose, sodium carboxymethyl cellulose, microcrystalline cellulose, polyethylene glycol, polyethylene oxide, polypropylene glycol;
- disintegrants, e.g. agar, alginic acid or its sodium salt, carboxymethylcellulose calcium and sodium, cellulose microcrystalline and powdered, chitosan, colloidal silicon dioxide, starch, pregelatinized starch, hydroxypropyl starch, sodium starch glycolate, croscarmellose sodium, crospovidone, guar gum, low-substituted hydroxypropyl cellulose, methylcellulose or effervescent mixtures; and/or
- absorbents, colorants, flavours and/or sweeteners.

A thorough discussion of pharmaceutically acceptable excipients is available in Gennaro, *Remington: The Science and Practice of Pharmacy* 2000, 20th edition (ISBN: 0683306472).

Accordingly, in one embodiment, the present invention provides a pharmaceutical composition comprising coated particles or microparticles and a pharmaceutically acceptable excipient.

Oral Administration

The coated particles or microparticles of the invention are preferably administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, tablets, solid particulates or microparticulates, semi-solid and liquid (including multiple phases or dispersed systems); soft or hard capsules containing multi- or nano-particulates, liquids (e.g. aqueous solutions), emulsions or powders; lozenges (including liquid-filled); chews; gels; jellies; fast dispersing dosage forms; films; ovules; sprays; and buccal/mucoadhesive patches. The coated microparticles of the invention are preferably part of liquid formulations for oral administration.

Formulations suitable for oral administration may also be designed to deliver the active pharmaceutical ingredient contained in the coated particles or microparticles in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups, drops, and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

The formulations containing the coated particles or microparticles may be easy to swallow or to be able to improve the swallowing process in patients with swallowing difficulties. The swallowing process is modulated by the nervous inputs generated from sensory receptors in the oral, pharyngeal and laryngeal regions via trigeminal, glossopharyngeal and vagus nerves. Taste, thermal and chemical properties of the ingested fluid act as "alerting" stimuli of these nerves and can affect swallowing activities. Liquids of sour taste stimulate stronger swallowing responses and improve oropharyngeal swallowing efficiency in patients who have a difficulty in swallowing (dysphagia). Pharmaceutical acceptable acidifiers can be added to the liquid formulation to generate sour tastes, including citric acid, acetic acid, calcium acetate, lactic acid, malic acid, fumaric acid and tartaric acid. The concentration of the acidifiers allows the generation of a pH level below 4.5, preferable pH 2 to 3.5. The concentration ranges from 1-20% w/v of the acids, preferably 0.0004-5% w/v. Natural occurring fruit juice and their extracts can be used as alternatives to the acids, including lemon, raspberry, orange, grapefruit juice. These can be used at concentration range 5-100% v/v, preferably 10-50% v/v.

Thermal stimulation in the form of a cold temperature applied to the oral and pharyngeal mucosa can produce the swallowing reflex and improve safe swallowing in dysphagic patients. The combination of cold temperature and sour taste enhances the effect of the individual stimulus. The temperature to be effective for such stimulation is in a range of 0-15° C., preferably, 0-8° C. The liquid formulation is prechilled to the target temperature before administration to patients to achieve such effect. Alternatively, mint-based flavours stimulate ion channel receptors in the sensory neurons, which lead to the perception of cold. Pharmaceutically acceptable mint-based flavours can be included in the formulation to achieve this effect, including peppermint flavour and spearmint flavour. These can be natural flavours extracted from essential oil or artificial mint flavours. Natural or synthetic compounds that can give a minty taste can be included such as menthol, menthones, menthyl acetate and mint terpenes. These flavours can be added at 0.1-5% w/v. Other pharmaceutically acceptable excipients that have a cooling effect in the mouth can be added in the formulation. An example of such excipients is mannitol. This can be used at a concentration of 1-50% w/v, preferably 1-20% w/v.

Beneficial effects of carbonated water were observed in patients with dysphagia to improve swallowing performance and reduce the risk of aspiration/penetration. The $CO_2$ dissolved in carbonated water is converted to carbonic acid which excites trigeminal neurons in the oral cavity and signals oral irritation. This intense oral sensory input, in turn, triggers stronger swallowing response in patients with dysphagia. An acid component and an alkaline component are included in the formulation to release $CO_2$ once in contact with aqueous solution. The acids that can be used include benzoic acid, malonic acid, tartartic acid, phthalic acid, barbituric acid, cinnamic acid, glutaric acid, hexanoic acid, malic acid, folic acid, propanoic acid, glycolic acid, stearic acid, trifluoroacetic acid, scorbic acid, citric acid, isocitric acid, succinic acid, glutaric acid, azelaic acid, benzoic acid, fumaric acid, adipic acid, gluconic acid, lactic acid, oleic acid, propiolic acid, uric acid, acetic acid, gallic acid, lauric acid, caprylic acid, caprinic acid, and myristic acid. The alkaline component includes sodium bicarbonate, sodium carbonate, sodium sesiquicarbonate, potassium bicarbonate and potassium carbonate. The concentration of the alkaline component is in the range of 1-20% w/v, and the concentration of the acid component is adjusted accordingly to ensure the liberation of $CO_2$. The stimuli of sour taste, cold temperature and carbonation can be applied to the formulation alone or as a combination of two or three factors.

Aspiration of liquids in patients with dysphagia is caused by inadequate protection of the airway during swallowing. Increasing liquid viscosity slows the oropharyngeal transit of the liquid and prevents the premature emptying from the mouth before the pharyngeal swallow response to protect the airway. The consistency of liquids can be described as thin (1-50 cp), nectar-thick (51-350 cp), honey-thick (351-1,750 cp) and spoon-thick (>1,750 cp) based on their viscosity range. Both honey-thick and nectar-thick liquids are able to significantly reduce the risk of aspiration in dysphagia patients compared to thin liquid. Pharmaceutically acceptable thickening agents are added to the formulation to modify the viscosity of the final suspension. These include starch and derivatives, alginin, guar gum, locust bean gum, xanthan gum, agar, gelatin, carrageenan, powdered cellulose, carbomers, alginic acid, sodium alginate, methylcellulose, hydroxyethylcellulose, carboxymethylcellulose, sodium carboxymethylcellulose, microcrystalline cellulose, hypromellose, acacia, tragacanth, bentonite, polyvinyl alcohol, polyvinyl pyrrolidone and colloidal silicon dioxide. The preferred thickening agent for this invention are hypromellose and xanthan gum. Commercially available starch and gum based thickening agents used for dysphagia management can also be added to the formulation to achieve the same effect. These include "Pregel", "Karicare", "Liquithick", "Nutilis", "Thicken Up", "Super Col-U", "Instant Carobel", "QuickThik", "RD Thickener", "Easy Thick", "ThickPlus", "Keltrol", "Guarcol", "Viscaid" and "Thick & Easy". The thickeners are used at concentration range of 0.05-20% w/v. The desired viscosity of the final liquid is in the range of 50-2000 cp.

The suspension can be prepared to a bulk volume for multiple doses or can be supplied as a single use dose. The volume of a single dose of the suspension is designed to accommodate the swallowing volume of patients with dysphagia. A single swallow volume of liquid in patients with dysphagia is approximately 10 ml which is about half the volume of a healthy human. Increasing the volume of a swallow from 5 to 20 ml increases the risk of aspiration in these patients. The ideal volume of a single dose of the suspension is in the range of 1-20 ml and preferably 5-10 ml.

Other pharmaceutically acceptable excipients that can be used in the formulation include solvents, preservatives, flavours and sweeteners. Water is the most desirable solvent for the suspension. Other pharmaceutically acceptable solvents can be used alone or as co-solvents including propylene glycol, glycerol, low molecular weight polyethylene glycol, and edible oils derived from animal or plant sources, such as corn oil, coconut oil, lemon oil, orange oil, olive oil, peanut oil, sunflower oil, soybean oil, sesame oil and nut oils.

It is preferred that preservatives are not used in the formulation. However, in cases where the suspension is prepared for multiple uses, preservatives may be included in the formulation. Pharmaceutically acceptable preservatives include chlorocresol, benzalkonium, benzoic acid, benzyl alcohol, methyl paraben, butyl paraben, ethyl paraben, propyl paraben, potassium sorbate, propionic acid, sodium benzoate, sorbic acid, propylene glycol. These may be used at concentrations from 0.01% to 5% w/v.

Sweeteners can be used to improve the taste and palatability of the suspension and can be used alone or as a mixture. Pharmaceutically acceptable sweeteners can be used including natural sugars and artificial sweeteners, such as glucose, fructose, xylose, ribose, mannose, dextrose, sucrose, maltose, galactose, sorbitol, xylitol, mannitol, glycerol, sucralose, saccharin and the corresponding sodium, potassium or calcium salt, cyclamate and the corresponding sodium or calcium salt, aspartame, acesulfame and potassium acesulfame. These are used in the formulation from 0.01 to 70% w/v, preferably 0.2-20% w/v.

Flavouring agents that can be used in the formulation include those from natural sources and artificial flavours. Some examples are mint flavours, strawberry flavours, lemon flavours, vanilla flavours, orange flavours, banana flavours, corn flavours, bubblegum flavours and berry flavours.

Although the invention has been described in the context of coating particles comprising an API to provide a modified-release coating, it is anticipated that the process of the invention could be used to coat other types of particle to provide other types of coating.

Enteral Administration

For patients with severe dysphagia or patients who are critically ill and cannot have oral intake at all (such as patients in intensive care units), enteral feeding tubes are commonly used for medicine administration. The coated microparticles of the invention may also be administered via enteral feeding tubes, preferably as part of a liquid formulation. The formulations suitable for enteral administration may be the same as the formulations suitable for oral administration discussed above.

Other Modes of Administration

The coated particles or microparticles of the invention may also be administered by other modes of administration. For example, the coated particles or microparticles may be administered by intranasal or inhaled administration, applications to skin and mucosal membranes or by rectal or vaginal administration.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

The following Examples are intended to illustrate the invention and are not to be construed as being limitations thereon.

Materials and Methods

1. Materials

Core: microspheres of microcrystalline cellulose, Cellets® 90 (diameter 63-90 μm), Cellets® 100 (diameter 125-180 μm) and Cellets® 1000 (diameter 500-750 μm), IPC Process-Centre GmbH & Co API: metoprolol succinate, Sinobio Chemistry Co. Ltd.; gliclazide, Sinobio Chemistry Co. Ltd. Polymers: Eudragit® RS 30D, RL 30D and NM 30D (30% aqueous dispersion, referred to as Eudragit® RS, RL and NM), Evonik Industries GmbH; hydroxypropyl methylcellulose (Methocel E5), Colorcon.

Glidants: glycerol monostearate (GMS, IMWITOR 900K), Cremer Oleo GmbH &Co.; magnesium Stearate, Acros Organics; silicon dioxide (Aerosil® 200 Pharma), Evonik Industries GmbH; talc, BDH Chemicals.

Other materials: triethyl citrate (TEC), polysorbate 80 (Tween 80), sodium phosphate monobasic dihydrate, sodium phosphate dibasic dodecahydrate from Sigma-Aldrich Co.

2. Methods 2.1 Loading Cellets® Cores with Metoprolol Succinate or Gliclazide

Cellets® 90, 100 and 1000 (150 g) was sprayed with metoprolol succinate solution or gliclazide suspension according to the Formulation A and B in Table 1, in a fluidised bed coater (Mini-Glatt, Glatt GmbH). Coating process parameters are shown in Table 2. Drug loading was complete until 50-400% weight gain was achieved. Talc was added to the formulation when coating Cellets® 90.

TABLE 1

Formulation composition for loading metoprolol succinate

| Ingredients | Formulation A Concentration % w/w | Formulation B Concentration % w/w |
|---|---|---|
| Metoprolol succinate | 20-40 | 0 |
| Gliclazide | 0 | 10 |
| Methocel E5 | 1-5 | 1 |

TABLE 1-continued

Formulation composition for loading metoprolol succinate

| Ingredients | Formulation A Concentration % w/w | Formulation B Concentration % w/w |
|---|---|---|
| Talc | 0-20 | 2 |
| Deionised water | 75 | 87 |
| Total | 100 | 100 |

TABLE 2

Coating process parameters for different formulations

| Parameters | Drug Loading | Eudragit ® RS/RL formulations | Eudragit ® NM formulations |
|---|---|---|---|
| Inlet Air Temp. (° C.). | 55-75 | 35-45 | 20-30 |
| Product Temp. (° C.) | 30-50 | 26-30 | 18-20 |
| Inlet Air Flow Rate (m³/hr) | 16 | 16-18 | 18 |
| Atomisation Pressure (bar) | 1.5-2.0 | 1.5-2.0 | 1.5-2.0 |
| Spray Rate (g/min) | 2.4 | 1.1-2.5 | 1.8-2.5 |

2.2 Polymer Coating of Cellets® Cores 2.2.1 Eudragit® RS/RL Coating with GMS as Anti-Tacking Agent in the Formulation Cellets® 100 (150 g) was coated with Eudragit® RS/RL with GMS as anti-tacking agent in the formulation, in a fluidised bed coater (Mini-Glatt, Glatt GmbH). The coating formulation is shown in Table 3 and coating process parameters are shown in Table 2. Two batches of coating were conducted using spray rate 1.1 g/min (Formulation C) and 1.6 g/min (Formulation D). Coating process was completed until 40% weight gain was achieved.

TABLE 3

Coating formulation using Eudragit ® RS/RL and GMS as anti-tacking agent

| Ingredients | Formulation C—H Quantity (g) |
|---|---|
| Eudragit ® RS 30 D (30% dispersion) | 202.5 |
| Eudragit ® RL30 D (30% dispersion) | 22.5 |
| Polysorbate 80 (Tween 80) | 5.9 |
| Triethyl Citrate (TEC) | 13.5 |
| Glycerol Monosterate | 13.5 |
| Water | 408.6 |
| Total solution | 666.6 |

Using the same coating formulation (Table 3) and coating process parameters (Table 2), different dry powder glidants were introduced to the processing column during coating every 30 min. The total quantity of dry powder added was 4% w/w based on dry polymer. The dry powder glidants used include magnesium stearate (Formulation E) and Aerosil® 200 Ph (Formulation F). The spray rate for Formulations E and F was 1.1 g/min. For magnesium stearate as dry powder, coating batches were also conducted at spray rate 1.6 g/min and magnesium stearate was added as dry powder every 30 min (Formulation G) and 15 min (Formulation H). The total quantities of dry powder glidants added to Formulations G and H are 3% and 6% based on dry polymer respectively.

2.2.2 Eudragit® RS/RL Coating with Aerosil® 200 pH as Anti-Tacking Agent in the Formulation Cellets® 100 (150 g) was coated with Eudragit® RS/RL with Aerosil® 200 Ph as anti-tacking agent in the formulation (Formulation I), in a fluidised bed coater (Mini-Glatt, Glatt GmbH). The coating formulation is shown in Table 4 and coating process parameters are shown in Table 2. The spray rate was 2.4 g/min. Coating process was completed until 40% weight gain was achieved.

TABLE 4

Coating formulation using Eudragit ® RS/RL and Aerosil ® 200 Ph as anti-tacking agent

| Ingredients | Formulation I, J Quantity (g) |
|---|---|
| Eudragit ® RS 30 D (30% suspension) | 202.5 |
| Eudragit ® RL30 D (30% suspension) | 22.5 |
| Polysorbate 80 (Tween 80) | 5.9 |
| Triethyl Citrate (TEC) | 13.5 |
| Aerosil ® 200 Ph | 20.3 |
| Water | 408.6 |
| Total solution | 673.3 |

Using the same coating formulation (Table 4), the same coating process parameters (Table 2) and the same spray rate (2.4 g/min), magnesium stearate was introduced as dry powder glidant to the processing column during coating every 15 min (Formulation J). The total quantity of dry powder added was 6% w/w based on dry polymer.

2.2.3 Eudragit® RS/RL Coating with Talc as Anti-Tacking Agent in the Formulation Cellets® 100 (150 g) was coated with Eudragit® RS/RL with talc as anti-tacking agent in the formulation (Formulation K), in a fluidised bed coater (Mini-Glatt, Glatt GmbH). The coating formulation is shown in Table 5 and coating process parameters are shown in Table 2. The spray rate was 1.9 g/min. Coating process was completed until 40% weight gain was achieved.

TABLE 5

Coating formulation using Eudragit ® RS/RL and talc as anti-tacking agent

| Ingredients | Formulation K, L Quantity (g) |
|---|---|
| Eudragit ® RS 30 D (30% suspension) | 202.5 |
| Eudragit ® RL30 D (30% suspension) | 22.5 |
| Triethyl Citrate (TEC) | 13.5 |
| Talc | 67.5 |
| Water | 684.0 |
| Total solution | 990.0 |

Using the same coating formulation (Table 5), the same coating process parameters (Table 2) and the same spray rate (1.9 g/min), magnesium stearate was introduced as dry powder glidant to the processing column during coating every 15 min (Formulation L). The total quantity of dry powder added was 10% w/w based on dry polymer.

2.2.4 Eudragit® NM Coating with Talc as Anti-Tacking Agent in the Formulation

Cellets® 100 (150 g) was coated with Eudragit® NM with talc as anti-tacking agent in the formulation (Formulation M), in a fluidised bed coater (Mini-Glatt, Glatt GmbH). The coating formulation is shown in Table 6 and coating process parameters are shown in Table 2. The spray rate was 2.0 g/min. Coating process was completed until 40% weight gain was achieved.

TABLE 6

Coating formulation using Eudragit® NM and talc as anti-tacking agent

| Ingredients | Formulation M, N Quantity (g) |
| --- | --- |
| Eudragit® NM 30 D (30% suspension) | 225.0 |
| Talc | 67.5 |
| Water | 607.5 |
| Total solution | 900.0 |

Using the same coating formulation (Table 6), the same coating process parameters (Table 2) and the same spray rate (2.0 g/min), magnesium stearate was introduced as dry powder glidant to the processing column during coating every 15 min (Formulation N). The total quantity of dry powder added was 9% w/w based on dry polymer.

2.3 Polymer Coating of Drug-Loaded Cellets®

Metoprolol succinate loaded Cellets® 1000 (50% drug loading) were coated using Eudragit® NM with talc as anti-tacking agent in the formulation, with and without additional magnesium stearate as dry powder (Formulations N and M respectively). Coating process parameters are shown in Table 2 and the spray rate was 2.0 g/min. Polymer coating levels were achieved at 20, 30 and 40% weight gain. Coated particles were cured at 40° C. for 24 hours.

Metoprolol succinate loaded Cellets® 100 (400% drug loading) were coated using Eudragit® NM, talc as anti-tacking agent in the formulation, with additional magnesium stearate as dry powder (Formulation N). Coating process parameters are shown in Table 2 and the spray rate was 2.0 g/min. Polymer coating levels were achieved at 100, 135 and 200% weight gain. Coated particles were cured at 40° C. for 24 hours.

Metoprolol succinate loaded Cellets® 90 (320% drug loading) were coated using Eudragit® NM, talc as anti-tacking agent in the formulation, with and without additional magnesium stearate as dry powder (Formulations N and M respectively). Coating process parameters are shown in Table 2 and the spray rate was 2.0 g/min. Polymer coating levels were achieved at 100, 150 and 200% weight gain. Coated particles were cured at 40° C. for 24 hours.

Gliclazide loaded Cellets® 100 (50% drug loading) were coated using Eudragit® NM, talc as anti-tacking agent in the formulation, with and without additional magnesium stearate as dry powder (Formulations N and M respectively). Coating process parameters are shown in Table 2 and the spray rate was 2.0 g/min. Polymer coating levels were achieved at 25% weight gain. Coated particles were cured at 40° C. for 24 hours.

2.4 Analysis of Coated Particles

At the end of each polymer coating trial, 1 g of Aerosil® 200 Ph was introduced to the processing column to separate the particles that are still free flowing in the processing column (FFP) and those that are not free flowing in the processing column or stuck at the "down-flow" bed (NFFP). The particle sizes of the FFP were then analysed using an analytical sieve shaker (AS200, Retsch® GmbH). Sieves with mesh size 90 µm, 125 µm, 180 µm, 250 µm, 355 µm, 710 µm were used. Microscopy of polymer coated particles were taken and the desired size range of the coated particles were decided based on no particle agglomeration in this range under microscope. Coating outcomes were analysed using the following equations:

$$\% \ FFP = \frac{\text{weight of } FFP}{\text{weight of total coated particles}} \times 100$$

$$\% \ NFFP = \frac{\text{weight of } NFFP}{\text{weight of total coated particles}} \times 100$$

$$\% \text{ particles in the desired size range} = \frac{\text{weight of particles in the desired size range}}{\text{weight of total } FFP} \times 100$$

$$\% \ yield = \frac{\% \text{ particles in the desired size range}}{100} \times \% \ FFP$$

2.5 Drug Release Tests

Drug release from polymer coated Cellets® containing metoprolol succinate were evaluated using USP Apparatus-II (Copley Scientific). The tests were conducted in 900 ml dissolution medium at 37±0.5° C. A paddle rotation speed of 50 rpm were used. The tests were conducted under sink conditions in 500 ml of pH 6.8 phosphate buffer solution. The quantity of metoprolol succinate released from the particles was determined using in-line UV-spectrophotometer (PG Instruments Ltd.) at wavelength 274 nm.

3 Results 3.1 Eudragit® RS/RL Coating with GMS as Anti-Tacking Agent in the Formulation Table 7 shows particle analysis results for Formulations C to H. Using GMS as anti-tacking agent for Eudragit® RS/RL coating, a large portion of particles were stuck at the "down flow" bed, with NFFP as 61% at spray rates 1.1 g/min (Formulation C). Adding dry powder glidants, magnesium stearate (Formulation E), and Aerosil® 200 Ph (Formulation F) significantly reduced the % NFFP to 1% and 4% respectively (at spray rate 1.1 g/min). % yield was increased from 39% to 99% for formulation with magnesium stearate as dry powder at spray rate 1.1 g/min.

When spray rate was increased from 1.1 g/min to 1.6 g/min, more particles were stuck at the "down flow" bed for the formulation without dry powder glidant (Formulation D), with % NFFP as 64% and % yield as 33%. Adding magnesium stearate every 30 min and 15 min (Formulations G and H respectively) significantly reduced % NFFP to 26% and 12% respectively and % yield was increased to 74% and 86% respectively.

TABLE 7

Particle analysis results for Formulations C to H

| Formulations | C | D | E | F | G | H |
|---|---|---|---|---|---|---|
| % FFP | 39 | 36 | 99 | 96 | 74 | 88 |
| % NFFP | 61 | 64 | 1 | 4 | 26 | 12 |
| % particles in the desired size range | 99 | 92 | 100 | 100 | 100 | 98 |
| % yield | 39 | 33 | 99 | 96 | 74 | 86 |

3.2 Eudragit® RS/RL Coating with Aerosil® 200 pH as Anti-Tacking Agent in the Formulation Table 8 shows particle analysis results for Formulations I and J. Using Aerosil® 200 Ph as anti-tacking agent for Eudragit® RS/RL coating (Formulation I), also a large portion of particles were stuck at the "down flow" bed, with % NFFP as 47% and % yield as 48%. Adding magnesium stearate every 15 min as dry powder during coating process (Formulation J) significantly reduced % NFFP to 1% and % yield was increased to 97%.

TABLE 8

Particle analysis results for Formulations I and J

| | Formulations | |
|---|---|---|
| | I | J |
| % FFP | 53 | 99 |
| % NFFP | 47 | 1 |
| % particles in the desired size range | 91 | 98 |
| % yield | 48 | 97 |

3.3 Eudragit® RS/RL Coating with Talc as Anti-Tacking Agent in the Formulation

Table 9 shows particle analysis results for Formulations K and L. Using talc as anti-tacking agent for Eudragit® RS/RL coating (Formulation K), also a large portion of particles were stuck at the "down flow" bed, with % NFFP as 68% and % yield as 26%. Adding magnesium stearate every 15 min as dry powder during coating process (Formulation L) significantly reduced % NFFP to 11% and % yield was increased to 88%.

TABLE 9

Particle analysis results for Formulations K and L

| | Formulations | |
|---|---|---|
| | K | L |
| % FFP | 32 | 89 |
| % NFFP | 68 | 11 |
| % particles in the desired size range | 81 | 99 |
| % yield | 26 | 88 |

3.4 Eudragit® NM Coating with Talc as Anti-Tacking Agent in the Formulation

Table 10 shows particle analysis results for Formulations M and N. Using talc as anti-tacking agent for Eudragit® NM coating (Formulation M), also a large portion of particles were stuck at the "down flow" bed, with % NFFP as 72% and % yield as 27%. Adding magnesium stearate every 15 min as dry powder during coating process (Formulation N) significantly reduced % NFFP to 10% and % yield was increased to 88%.

TABLE 10

Particle analysis results for Formulations M and N

| | Formulations | |
|---|---|---|
| | M | N |
| % FFP | 28 | 90 |
| % NFFP | 72 | 10 |
| % particles in the desired size range | 95 | 98 |
| % yield | 27 | 88 |

3.5 Polymer Coating on Drug-Loaded Particles

Figure 2:
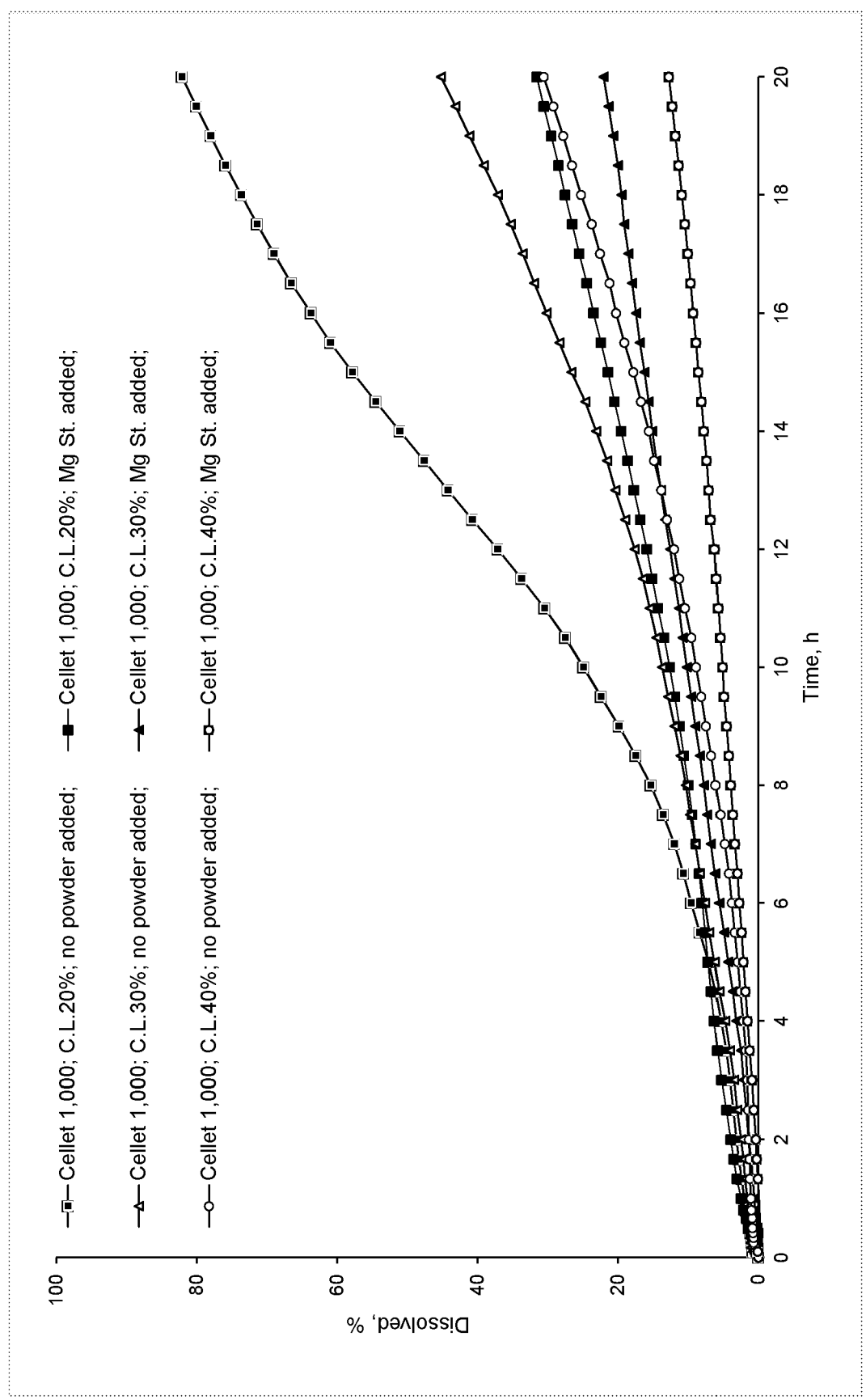
FIG. 2 illustrates a chart showing the drug release from 50% metoprolol succinate loaded Cellets® 1,000 which are coated with different coating levels (C.L.) with Eudragit® NM and with 100% talc as glidant, with and without magnesium stearate added as dry powder during coating process. Magnesium stearate is abbreviated as Mg St.

Cellets® 1000 was loaded with 50% (weigh gain) of metoprolol succinate and coated with Eudragit® NM. The % yield of the coating process was more than 99% with and without magnesium stearate dry powder addition. FIG. 2. shows drug release from coated particles of different coating levels (C.L.) with and without magnesium stearate added as dry powder during coating process (Formulation N and M). It can be seen that when magnesium stearate was added as dry powder during process it significantly decreased drug release rate at the same coating level.

FIG. 2 illustrates a chart showing drug release from 50% drug loaded Cellets® 1,000 which are coated with different coating levels (C.L.) with Eudragit® NM and with 100% talc as glidant. Magnesium stearate is abbreviated as Mg St.

Figure 3:
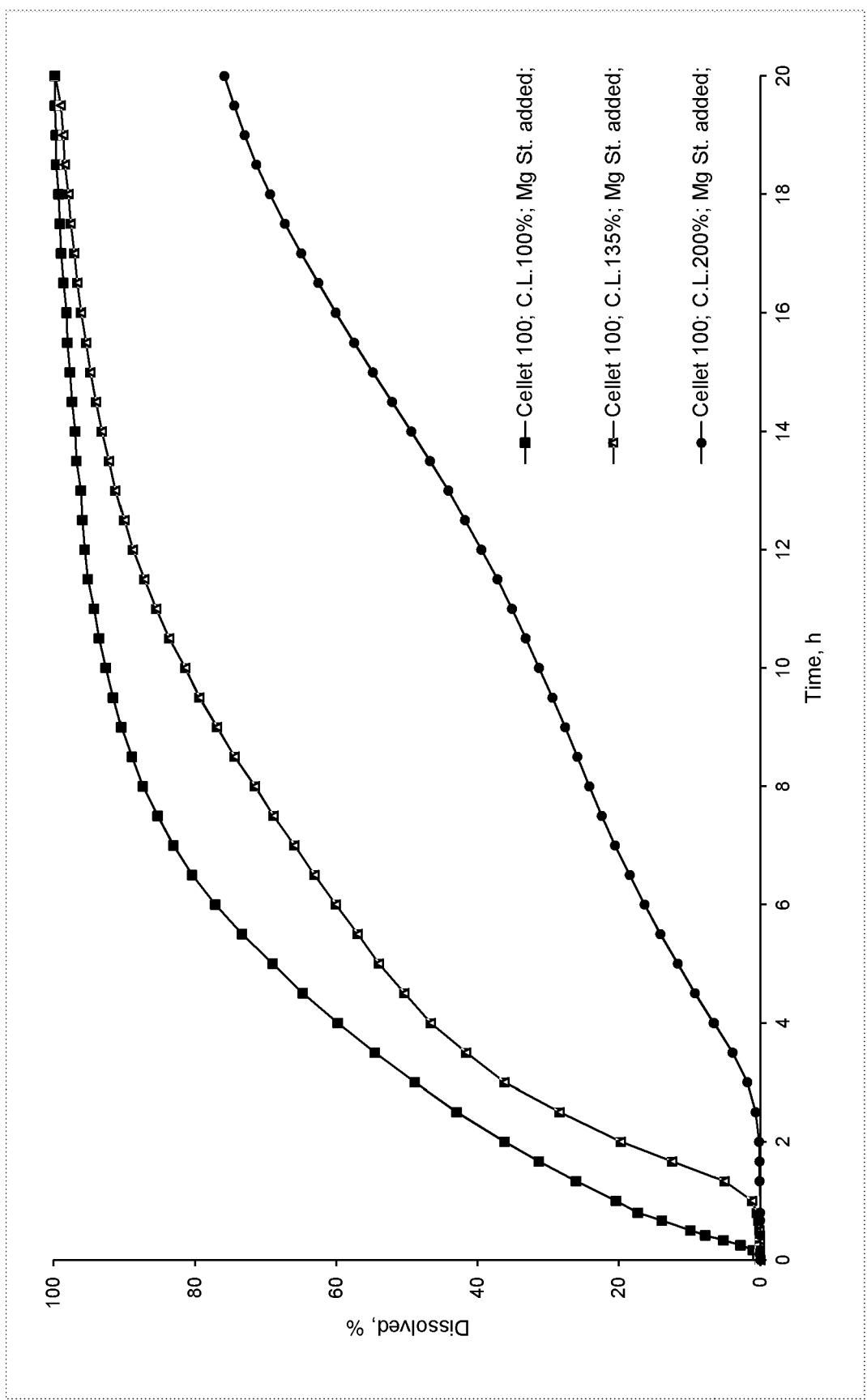
FIG. 3 illustrates a chart showing the drug release from 400% metoprolol succinate loaded Cellets® 100 which are coated with different coating levels (C.L.) with Eudragit® NM and with 100% talc as glidant. Magnesium stearate is abbreviated as Mg St.

Cellets® 100 was loaded with 400% (weigh gain) of metoprolol succinate and coated with Eudragit® NM. The % yield of the coating process was more than 99% with the addition of magnesium stearate dry powder during coating process. FIG. 3 shows drug release from coated particles of different coating levels (C.L.) with magnesium stearate added as dry powder during coating process (Formulation N).

FIG. 3 illustrates a chart showing drug release from 400% drug loaded Cellets® 100 which are coated with different coating levels (C.L.) with Eudragit® NM with 100% talc as glidant. Magnesium stearate is abbreviated as Mg St.

Figure 4:
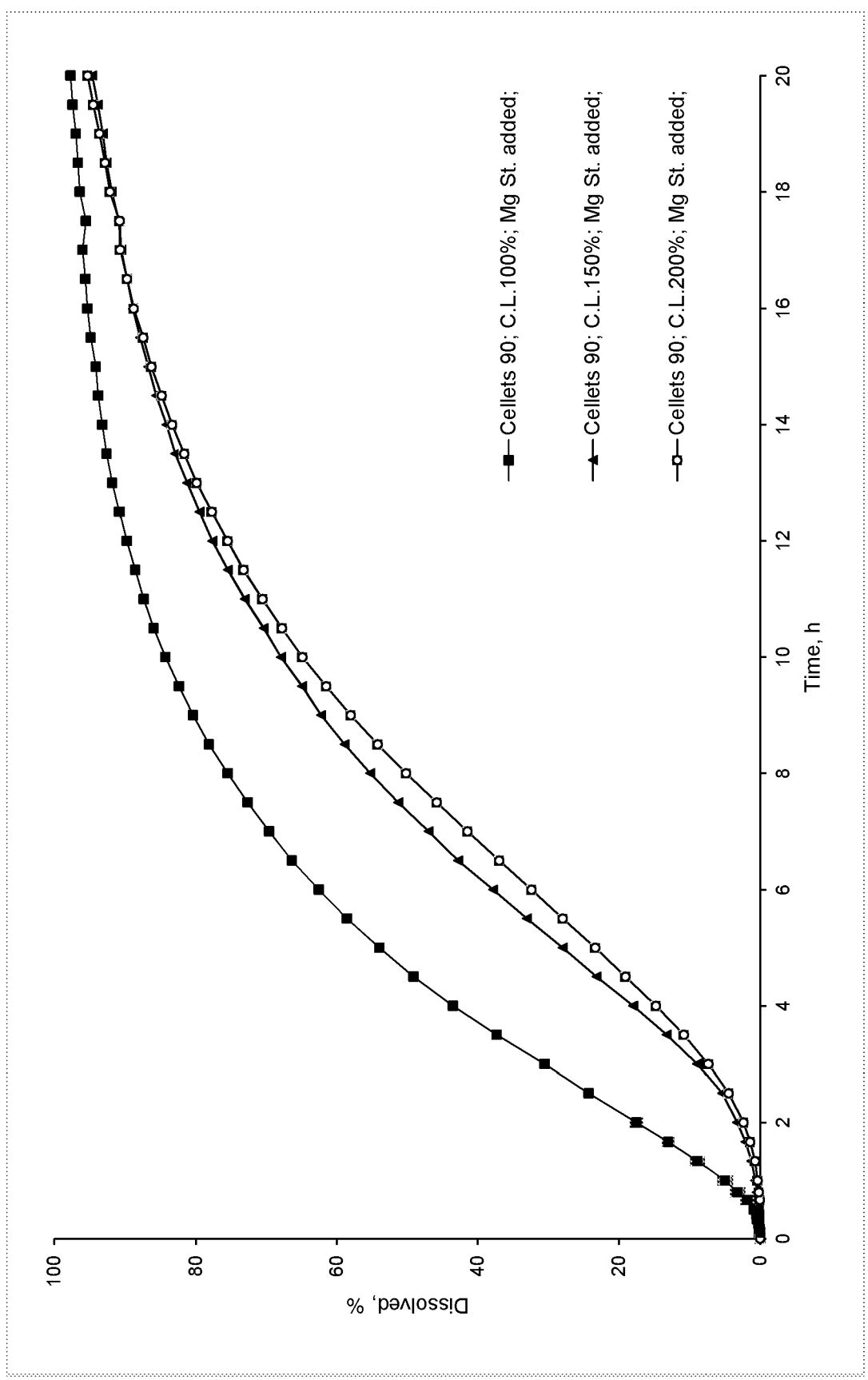
FIG. 4 illustrates a chart showing the drug release from 320% metoprolol succinate loaded Cellets® 90 which are coated with different coating levels (C.L.) with Eudragit® NM and with 100% talc as glidant. Magnesium stearate is abbreviated as Mg St.

Cellets® 90 was loaded with 320% (weigh gain) of metoprolol succinate and coated with Eudragit® NM. The formulation without the addition of magnesium stearate as dry powder could not be completed due to severe particle agglomeration and particles sticking at the down-flow bed. The % yield of the coating process with the addition of magnesium stearate as dry powder was 99%. FIG. 4 shows drug release from coated particles of different coating levels (C.L.) with magnesium stearate added as dry powder during coating process (Formulation N and M).

FIG. 4 illustrates a chart showing drug release from 320% drug loaded Cellets® 90 which are coated with different coating levels (C.L.) and with Eudragit® NM with 100% talc as glidant. Magnesium stearate is abbreviated as Mg St.

Cellets® 100 was loaded with 50% (weight gain) of gliclazide and coated with Eudragit® NM. The % yield of the coating process was more than 99% with magnesium stearate dry powder addition and was 72% without magnesium stearate dry powder addition. FIG. 5. shows drug release from coated particles at 25% coating level (C.L.) with and without magnesium stearate added as dry powder during coating process (Formulation N and M). It can be seen that when magnesium stearate was added as dry powder during process it significantly decreased drug release rate at the same coating level.

It will be understood that the invention has been described by way of example only and modifications may be made whilst remaining within the scope of the invention.

While the present invention has been illustrated by description of various embodiments and while those embodiments have been described in considerable detail, it is not the intention of Applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of Applicant's invention.

The invention claimed is:

1. A method for coating microparticles in a Wurster fluidized bed coater comprising a processing column, wherein the microparticles comprise an active pharmaceutical ingredient, the method comprising:
   (i) adding microparticles to the processing column to provide a fluidized stream of microparticles in the processing column;
   (ii) coating the microparticles by adding a liquid coating formulation to the processing column in a spray zone of the processing column through a first inlet that comprises at least one spray nozzle that is in a first region of the processing column; and
   (iii) adding a powdered glidant to the processing column in a drying zone or down-flow zone of the processing column through a second inlet that is in a second region of the processing column;
   wherein the first region of the processing column and the second region of the processing column are substantially separate from each other.

2. The method according to claim 1 wherein at least 80% w/w of the microparticles to be coated have a particle size range of 10-1000 μm or 10-350 μm or 10-200 μm.

3. The method according to claim 1 wherein the glidant is selected from the group consisting of talc, kaolin, bentonite, stearic acid, glycerol monostearate, zinc stearate, magnesium stearate, calcium stearate, aluminum monostearate, glyceryl stearate, glyceryl palmitostearate, sodium stearyl fumarate, magnesium silicate, calcium silicate, magnesium aluminum silicate, silicon dioxide, colloidal silicon dioxide, hydrophobic colloidal silica, aluminum oxide, magnesium oxide, titanium dioxide, calcium carbonate, magnesium carbonate, calcium phosphate, and combinations thereof.

4. The method according to claim 3 wherein the glidant is magnesium stearate or silicon dioxide or a combination of magnesium stearate and silicon dioxide.

5. The method according to claim 3 wherein the glidant is a combination of magnesium stearate and silicon dioxide.

6. The method according to claim 1 wherein the coating formulation comprises at least one polymer, wherein the powdered excipient is added in amounts of 0.1-50% or 0.5-20% or 0.5-10% w/w based on the weight of the at least one polymer in the coating formulation, and wherein the at least one polymer is dry.

7. The method according to claim 1 wherein the powdered glidant is dry.

8. The method according to claim 1 wherein the powdered glidant has a median particle size of greater than 0 μm to 200 μm, or 0.1-100 μm, or 1-50 μm, or about 10 μm.

9. The method according to claim 1 wherein the powdered glidant in step (iii) is added continuously or intermittently.

10. The method according to claim 1 wherein the coating formulation in step (ii) is added continuously.

11. The method according to claim 1 wherein the second inlet comprises at least one loading port.

12. The method according to claim 1 wherein the second inlet comprises at least one spray nozzle.

13. The method according to claim 1 wherein the coating formulation comprises a glidant.

14. The method according to claim 13 wherein the glidant is selected from the group consisting of talc, kaolin, bentonite, stearic acid, glycerol monostearate, zinc stearate, magnesium stearate, calcium stearate, aluminum monostearate, glyceryl stearate, glyceryl palmitostearate, sodium stearyl fumarate, magnesium silicate, calcium silicate, magnesium aluminum silicate, silicon dioxide, colloidal silicon dioxide, hydrophobic colloidal silica, aluminum oxide, magnesium oxide, titanium dioxide, calcium carbonate, magnesium carbonate, calcium phosphate, and combinations thereof.

15. Coated microparticles obtainable by the method according to claim 1.

16. The coated microparticles according to claim 15 wherein at least 80% w/w of the coated microparticles have a particle size range of 20-1200 μm, or 20-400 μm, or 20-250 μm.

17. The coated microparticles according to claim 15 wherein at least 80% w/w of the coated microparticles have a particle size range of 20-12000 μm.

18. The coated microparticles according to claim 15 wherein the coating is suitable for providing modified release of the active pharmaceutical ingredient.

19. A pharmaceutical composition comprising coated microparticles according to claim 15 and a pharmaceutically acceptable excipient.

20. The pharmaceutical composition according to claim 19 suitable for oral administration.

21. The pharmaceutical composition according to claim 19 wherein the coated microparticles are dispersed in a liquid medium.

22. The pharmaceutical composition according to claim 19 in the form of a powder for mixing with a liquid before administration.

23. A method for coating particles with a controlled drug release coating in a Wurster fluidized bed coater comprising a processing column, wherein the particles comprise an active pharmaceutical ingredient, the method comprising:
   (i) adding particles to the processing column to provide a fluidized stream of particles in the processing column;
   (ii) coating the particles with a controlled drug release coating by adding a controlled drug release liquid coating formulation in a spray zone of the processing column through at least one spray nozzle that is in a first region of the processing column; and
   (iii) adding a powdered glidant to the processing column in a drying zone or down-flow zone of the processing column through a second inlet that is in a second region of the processing column;
   wherein the first region of the processing column and the second region of the processing column are substantially separate from each other.

24. The method according to claim 23 wherein at least 80% w/w of the particles to be coated have a particle size range of 10-10,000 μm.

25. The method according to claim 23 wherein the glidant is selected from the group consisting of talc, kaolin, bentonite, stearic acid, glycerol monostearate, zinc stearate, magnesium stearate, calcium stearate, aluminum monostearate, glyceryl stearate, glyceryl palmitostearate, sodium stearyl fumarate, magnesium silicate, calcium silicate, magnesium aluminum silicate, silicon dioxide, colloidal silicon dioxide, hydrophobic colloidal silica, aluminum oxide, magnesium oxide, titanium dioxide, calcium carbonate, magnesium carbonate, calcium phosphate, and combinations thereof.

26. The method according to claim 25 wherein the glidant is magnesium stearate or silicon dioxide or a combination of magnesium stearate and silicon dioxide.

27. The method according to claim 25 wherein the glidant is a combination of magnesium stearate and silicon dioxide.

28. The method according to claim 23 wherein the coating formulation comprises at least one polymer, wherein the powdered excipient is added in amounts of 0.1-50% or 0.5-20% or 0.5-10% w/w based on the weight of the at least one polymer in the coating formulation, and wherein the at least one polymer is dry.

29. The method according to claim 23 wherein the powdered glidant is dry.

30. The method according to claim 23 wherein the powdered glidant has a median particle size of greater than 0 µm to 200 µm, or 0.1-100 µm, or 1-50 µm, or about 10 µm.

31. The method according to claim 23 wherein the powdered glidant in step (iii) is added continuously or intermittently.

32. The method according to claim 23 wherein the coating formulation in step (ii) is added continuously.

33. The method according to claim 23 wherein the second inlet comprises at least one loading port.

34. The method according to claim 23 wherein the second inlet comprises at least one spray nozzle.

35. The method according to claim 23 wherein the coating formulation comprises a glidant.

36. The method according to claim 35 wherein the glidant is selected from the group consisting of talc, kaolin, bentonite, stearic acid, glycerol monostearate, zinc stearate, magnesium stearate, calcium stearate, aluminum monostearate, glyceryl stearate, glyceryl palmitostearate, sodium stearyl fumarate, magnesium silicate, calcium silicate, magnesium aluminum silicate, silicon dioxide, colloidal silicon dioxide, hydrophobic colloidal silica, aluminum oxide, magnesium oxide, titanium dioxide, calcium carbonate, magnesium carbonate, calcium phosphate, and combinations thereof.

37. Coated particles obtainable by the method according to claim 23.

38. The coated particles according to claim 37 wherein at least 80% w/w of the coated particles have a particle size range of 20-1200 µm, or 20-400 µm, or 20-250 µm.

39. The coated particles according to claim 37 wherein at least 80% w/w of the coated particles have a particle size range of 20-12000 µm.

40. The coated particles according to claim 37 wherein the coating is suitable for providing modified release of the active pharmaceutical ingredient.

41. A pharmaceutical composition comprising coated particles according to claim 37 and a pharmaceutically acceptable excipient.

42. The pharmaceutical composition according to claim 41 suitable for oral administration.

43. The pharmaceutical composition according to claim 41 wherein the coated particles are dispersed in a liquid medium.

44. The pharmaceutical composition according to claim 41 in the form of a powder for mixing with a liquid before administration.

45. The method according to claim 1 wherein the first region of the processing column is a region of the processing column adjacent to the spray nozzle.

46. The method according to claim 23 wherein the first region of the processing column is a region of the processing column adjacent to the spray nozzle.

* * * * *